(12) United States Patent
Weaver et al.

(10) Patent No.: US 9,821,107 B2
(45) Date of Patent: Nov. 21, 2017

(54) DIALYSIS SYSTEMS AND METHODS

(71) Applicant: Fresenius Medical Care Holdings, Inc., Waltham, MA (US)

(72) Inventors: Colin Weaver, Pleasanton, CA (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 6 days.

(21) Appl. No.: 14/965,103

(22) Filed: Dec. 10, 2015

(65) Prior Publication Data
US 2016/0114092 A1    Apr. 28, 2016

Related U.S. Application Data

(60) Division of application No. 13/520,082, filed as application No. PCT/US2011/020537 on Jan. 7, (Continued)

(51) Int. Cl.
*A61M 1/36* (2006.01)
*G01F 23/296* (2006.01)
(Continued)

(52) U.S. Cl.
CPC ........ *A61M 1/3627* (2013.01); *A61M 1/1601* (2014.02); *A61M 1/3607* (2014.02); *A61M 1/3624* (2013.01); *A61M 1/3639* (2013.01); *A61M 1/3641* (2014.02); *G01F 23/296* (2013.01); *G01L 19/0092* (2013.01); *A61M 1/16* (2013.01); *A61M 2202/0413* (2013.01); *A61M 2205/15* (2013.01); *A61M 2205/18* (2013.01); *A61M 2205/3306* (2013.01); *A61M 2205/3331* (2013.01); *A61M 2205/3334* (2013.01); *A61M 2205/3375* (2013.01);
(Continued)

(58) Field of Classification Search
None
See application file for complete search history.

(56) References Cited

U.S. PATENT DOCUMENTS

| | | | |
|---|---|---|---|
| 3,946,731 | A | 3/1976 | Lichtenstein |
| 3,982,538 | A | 9/1976 | Sharpe |

(Continued)

FOREIGN PATENT DOCUMENTS

| | | |
|---|---|---|
| DE | 102005001779 | 9/2006 |
| EP | 0327136 | 8/1989 |

(Continued)

OTHER PUBLICATIONS

Angie's List: "Does shutting furnace vents improve energy efficiency", http://www.angieslist.com/articles/does-shutting-furnace-vents-improve-energy-efficiency.htm, Nov. 18, 2016, 4 pages.

(Continued)

*Primary Examiner* — Dirk Bass
(74) *Attorney, Agent, or Firm* — Fish & Richardson P.C.

(57) ABSTRACT

This invention relates to dialysis systems and methods. In some implementations, a method includes applying vacuum pressure to a device of a dialysis system, and then determining, based on a detected fluid level or measured pressure, whether the device is functioning properly.

22 Claims, 9 Drawing Sheets

Related U.S. Application Data 2011, now Pat. No. 9,220,832, which is a continuation-in-part of application No. 12/683,980, filed on Jan. 7, 2010, now Pat. No. 8,500,994.

(51) Int. Cl.
*G01L 19/00* (2006.01)
*A61M 1/16* (2006.01)

(52) U.S. Cl.
CPC . *A61M 2205/3379* (2013.01); *A61M 2205/50* (2013.01); *A61M 2205/505* (2013.01); *A61M 2205/702* (2013.01); *A61M 2205/707* (2013.01); *A61M 2205/7536* (2013.01)

(56) References Cited

U.S. PATENT DOCUMENTS

| | | | |
|---|---|---|---|
| 3,985,135 A | 10/1976 | Carpenter et al. | |
| 3,996,027 A | 12/1976 | Schnell et al. | |
| 4,014,206 A | 3/1977 | Taylor | |
| 4,026,669 A | 5/1977 | Leonard et al. | |
| 4,061,031 A | 12/1977 | Grimsrud | |
| 4,137,160 A | 1/1979 | Ebling et al. | |
| 4,187,057 A | 2/1980 | Xanthopoulos | |
| 4,231,370 A | 11/1980 | Mroz et al. | |
| 4,370,983 A | 2/1983 | Lichtenstein | |
| 4,459,139 A | 7/1984 | vonReis et al. | |
| 4,488,961 A | 12/1984 | Spencer | |
| 4,530,759 A | 7/1985 | Schal | |
| 4,572,724 A | 2/1986 | Rosenberg et al. | |
| 4,590,227 A | 5/1986 | Nakamura et al. | |
| 4,622,032 A | 11/1986 | Katsura et al. | |
| 4,643,713 A | 2/1987 | Viitala | |
| 4,662,906 A | 5/1987 | Matkovich et al. | |
| 4,695,385 A | 9/1987 | Boag | |
| 4,702,675 A | 10/1987 | Aldrovandi et al. | |
| 4,702,829 A | 10/1987 | Polaschegg et al. | |
| 4,795,457 A | 1/1989 | Cooney | |
| 4,888,004 A | 12/1989 | Williamson et al. | |
| 4,997,464 A | 3/1991 | Kopf | |
| 5,061,236 A | 10/1991 | Sutherland et al. | |
| 5,330,425 A | 7/1994 | Utterberg | |
| 5,425,173 A | 6/1995 | Moss et al. | |
| 5,441,636 A | 8/1995 | Chevallet et al. | |
| 5,460,490 A | 10/1995 | Carr et al. | |
| 5,498,338 A | 3/1996 | Kruger et al. | |
| 5,540,265 A | 7/1996 | Polaschegg et al. | |
| 5,578,070 A | 11/1996 | Utterberg | |
| 5,580,460 A | 12/1996 | Polaschegg | |
| 5,591,344 A | 1/1997 | Kenley et al. | |
| 5,614,677 A | 3/1997 | Wamsiedler et al. | |
| 5,628,908 A | 5/1997 | Kamen et al. | |
| 5,643,205 A | 7/1997 | Utterberg | |
| 5,651,893 A | 7/1997 | Kenley et al. | |
| 5,674,390 A | 10/1997 | Matthews et al. | |
| 5,674,404 A | 10/1997 | Kenley et al. | |
| 5,690,831 A | 11/1997 | Kenley et al. | |
| 5,711,883 A | 1/1998 | Folden et al. | |
| 5,714,060 A | 2/1998 | Kenley et al. | |
| 5,725,776 A | 3/1998 | Kenley et al. | |
| 5,788,671 A | 8/1998 | Johnson | |
| 5,849,065 A | 12/1998 | Wojke | |
| 5,863,421 A | 1/1999 | Peter et al. | |
| 5,928,177 A | 7/1999 | Brugger et al. | |
| 5,938,634 A | 8/1999 | Packard | |
| 5,989,423 A | 11/1999 | Kamen et al. | |
| 6,179,801 B1 | 1/2001 | Holmes et al. | |
| 6,196,987 B1 | 3/2001 | Holmes et al. | |
| 6,200,287 B1 | 3/2001 | Keller et al. | |
| 6,231,537 B1 | 5/2001 | Holmes et al. | |
| 6,234,989 B1 | 5/2001 | Brierton et al. | |
| 6,280,406 B1 | 8/2001 | Dolecek et al. | |
| 6,336,916 B1 | 1/2002 | Bormann et al. | |
| 6,337,049 B1 | 1/2002 | Tamari | |
| 6,361,518 B1 | 3/2002 | Brierton et al. | |
| 6,383,158 B1 | 5/2002 | Utterberg et al. | |
| 6,409,696 B1 | 6/2002 | Toavs et al. | |
| 6,497,674 B1 | 12/2002 | Steele et al. | |
| 6,497,676 B1 | 12/2002 | Childers et al. | |
| 6,514,225 B1 | 2/2003 | Utterberg et al. | |
| 6,536,278 B1 | 3/2003 | Scagliarini | |
| 6,695,803 B1 | 2/2004 | Robinson et al. | |
| 6,725,726 B1 | 4/2004 | Adolfs et al. | |
| 6,730,055 B2 | 5/2004 | Bainbridge et al. | |
| 6,743,201 B1 | 6/2004 | Doenig et al. | |
| 6,755,801 B2 | 6/2004 | Utterberg et al. | |
| 6,764,460 B2 | 7/2004 | Dolecek et al. | |
| 6,773,426 B2 | 8/2004 | Tamari | |
| 6,790,195 B2 | 9/2004 | Steele et al. | |
| 6,852,090 B2 | 2/2005 | Burbank et al. | |
| 6,887,214 B1 | 5/2005 | Levin et al. | |
| 6,979,309 B2 | 12/2005 | Burbank et al. | |
| 7,021,148 B2 | 4/2006 | Kuhn et al. | |
| 7,115,107 B2 | 10/2006 | Delnevo et al. | |
| 7,198,751 B2 * | 4/2007 | Carpenter | A61M 1/101 210/645 |
| 7,238,164 B2 | 7/2007 | Childers et al. | |
| 7,476,209 B2 | 1/2009 | Gara et al. | |
| 7,517,387 B2 | 4/2009 | Chevallet et al. | |
| 7,603,907 B2 | 10/2009 | Reiter et al. | |
| 7,621,983 B2 | 11/2009 | Neri | |
| 7,871,391 B2 | 1/2011 | Folden et al. | |
| 7,892,331 B2 | 2/2011 | Childers et al. | |
| 7,892,332 B2 | 2/2011 | Prisco et al. | |
| 7,905,853 B2 | 3/2011 | Chapman et al. | |
| 8,110,104 B2 | 2/2012 | Crnkovich | |
| 8,142,653 B2 | 3/2012 | Beden et al. | |
| 8,663,463 B2 | 3/2014 | Weaver et al. | |
| 2002/0014462 A1 | 2/2002 | Muller | |
| 2002/0072718 A1 | 6/2002 | Brugger et al. | |
| 2002/0179527 A1 | 12/2002 | Yao | |
| 2004/0019312 A1 | 1/2004 | Childers et al. | |
| 2004/0238416 A1 | 12/2004 | Burbank et al. | |
| 2005/0054968 A1 | 3/2005 | Giannella | |
| 2005/0126998 A1 | 6/2005 | Childers | |
| 2005/0131332 A1 | 6/2005 | Kelly et al. | |
| 2005/0132826 A1 | 6/2005 | Teugels | |
| 2005/0230292 A1 | 10/2005 | Beden et al. | |
| 2007/0078369 A1 | 4/2007 | Tamari | |
| 2007/0086924 A1 | 4/2007 | Moses | |
| 2007/0106198 A1 | 5/2007 | Folden et al. | |
| 2007/0112297 A1 | 5/2007 | Plahey et al. | |
| 2007/0193940 A1 | 8/2007 | Duchamp et al. | |
| 2007/0269340 A1 | 11/2007 | Dannenmaier et al. | |
| 2008/0275364 A1 | 11/2008 | Conway et al. | |
| 2009/0012449 A1 | 1/2009 | Lee et al. | |
| 2009/0071911 A1 | 3/2009 | Folden et al. | |
| 2009/0084721 A1 | 4/2009 | Yardimci et al. | |
| 2009/0088675 A1 | 4/2009 | Kelly et al. | |
| 2009/0101576 A1 | 4/2009 | Rohde et al. | |
| 2009/0216211 A1 | 8/2009 | Beden et al. | |
| 2009/0320684 A1 | 12/2009 | Weaver et al. | |
| 2010/0133189 A1 | 6/2010 | Maierhofer et al. | |
| 2010/0206784 A1 | 8/2010 | Weaver et al. | |
| 2010/0222735 A1 | 9/2010 | Plahey et al. | |
| 2010/0292627 A1 | 11/2010 | Caleffi et al. | |
| 2011/0120946 A1 | 5/2011 | Levin et al. | |

FOREIGN PATENT DOCUMENTS

| | | |
|---|---|---|
| EP | 0458041 | 11/1991 |
| EP | 0728509 | 8/1996 |
| EP | 0887100 | 12/1998 |
| EP | 1529545 | 5/2005 |
| EP | 1547630 | 6/2005 |
| EP | 1728526 | 3/2008 |
| EP | 1894587 | 3/2008 |
| EP | 2226087 | 9/2010 |
| EP | 2521576 B1 | 8/2015 |
| JP | 2003180834 | 7/2003 |
| JP | 2005530543 | 10/2005 |
| JP | 2006263136 A | 10/2006 |
| JP | 2007130290 A | 5/2007 |
| WO | WO9640322 A3 | 12/1996 |

(56) References Cited

FOREIGN PATENT DOCUMENTS

| WO | WO9702056 A1 | 1/1997 |
|---|---|---|
| WO | WO0108722 A2 | 2/2001 |
| WO | WO0150949 A1 | 7/2001 |
| WO | WO0164312 A1 | 9/2001 |
| WO | WO0226286 A2 | 4/2002 |
| WO | WO04000391 A1 | 12/2003 |
| WO | WO2004069299 A2 | 8/2004 |
| WO | WO2005044340 A1 | 5/2005 |
| WO | WO2005044341 A1 | 5/2005 |
| WO | WO2005065745 A1 | 7/2005 |
| WO | WO2005077490 A1 | 8/2005 |
| WO | WO2007050211 A2 | 5/2007 |
| WO | WO2008002370 A2 | 3/2008 |

OTHER PUBLICATIONS

Merriam-Webster: "Definition of Vent by Merriam-Webster", http://www.merriam-webster.com/dictionary/vent, cited Nov. 18, 2016, 9 pages.
Communication of a Notice of Opposition for European Patent No. 2521576, dated Nov. 23, 2016.
Acu-men, Acute Dialysis Machine Operating Instructions, Software Version 1.0, Fresenius MY acu-men, Jan. 5, 1996, 146 pages.
Gambro®, "DEHP-Free Cartridge Blood Sets", © Nov. 2004, Gambro, Inc, Lakewood, CO, 4 pp.
Gambro®, Prisma® HF 1000, "For Increased Filtration Capacity", © Aug. 2001, Gambro Renal Products, Inc., Lakewood, CO, 2 pp.
Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.
Gambro®, "Prismaflex™, Anticipating Critical Care needs and taking our innovative response . . . to new heights", © 2004, Gambro Inc., Lakewood, CO, 8 pp.
International Search Report and Written Opinion; PCT/US06/36802; dated May 8, 2008.
International Search Report and Written Opinion; PCT/US2008/076830; dated Dec. 29, 2008.
Manns, Markus et al., "The acu-men: A new device for continuous renal replacement therapy in acute renal failure," Kidney International, vol. 54, pp. 268-274, 1998.
International Search Report and Written Opinion for PCT/US2011/020537, dated May 24, 2011.
Communication of a Notice of Opposition for European Patent No. 2521576, dated May 23, 2016.

\* cited by examiner

DIALYSIS SYSTEMS AND METHODS

CROSS-REFERENCE TO RELATED APPLICATIONS

This application is a divisional of and claims priority under 35 U.S.C. §120 to U.S. Ser. No. 13/520,082, filed Sep. 18, 2012, which is a 371 of International application No. application No. PCT/US2011/020537, filed on Jan. 7, 2011, which is a continuation-in-part of U.S. Ser. No. 12/683,980, filed Jan. 7, 2010. The contents of these priority applications are hereby incorporated by reference in their entirety.

TECHNICAL FIELD

This invention relates to dialysis systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a method includes applying vacuum pressure to an air release device of a dialysis system. The air release device includes a vent. After applying the vacuum pressure to the air release device, a fluid level within the air release device is detected. Based on the fluid level within the air release device, it is determined whether the air release device is functioning properly.

In another aspect of the invention, a method includes applying vacuum pressure to a device of a dialysis system. The device includes a vent. After applying the vacuum pressure to the device, a pressure within a fluid line that is fluidly connected to the device is measured. Based on the measured pressure, it is determined whether the device is functioning properly.

In a further aspect of the invention, a method includes applying vacuum pressure to an air release device of a dialysis system. The air release device includes a vent. After applying the vacuum pressure to the air release device, a fluid level within the air release device is detected, and if the fluid level within the air release device exceeds a given level after applying the vacuum pressure to the air release device, a user is informed that the air release device is not functioning properly.

In an additional aspect of the invention, a method includes applying vacuum pressure to a device of a dialysis system. The device includes a vent. After applying the vacuum pressure to the device, a pressure within a fluid line that is fluidly connected to the device is measured, and if the measured pressure is less than a certain pressure, a user is informed that the device is not functioning properly.

In yet another aspect of the invention, a dialysis system includes an air release device with a vent, a level detector configured to detect a level of fluid within the air release device, and a control unit connected to the level detector. The control unit is configured to determine whether the air release device is functioning properly based on a detected fluid level within the air release device when vacuum pressure is applied to the air release device.

In a further aspect of the invention, a dialysis system includes a device with a vent, a fluid line fluidly connected to the device, a pressure sensor configured to measure pressure of fluid within the fluid line, and a control unit connected to the pressure sensor. The control unit is configured to determine whether the device is functioning properly based on a measured pressure of fluid within the fluid line when vacuum pressure is applied to the device.

Implementations can include one or more of the following features.

In some implementations, determining whether the air release device is functioning properly includes determining whether the vent of the air release device is functioning properly.

In certain implementations, the fluid level within the air release device is detected by a level detector of the dialysis system, and the level detector is positioned adjacent the air release device.

In some implementations, the level detector includes a transmitter configured to emit ultrasonic signals and a receiver adapted to receive ultrasonic signals.

In certain implementations, the level detector is connected to a control unit of the dialysis system in a manner such that signals related to the detected fluid level can be transmitted to the control unit.

In some implementations, applying vacuum pressure to the air release device includes closing off lines upstream and downstream of the air release device and activating a pump to draw fluid out of the air release device.

In certain implementations, closing off the line upstream of the air release device includes turning off a pump configured to circulate fluid through the air release device, and closing off the line downstream of the air release device includes clamping the line downstream of the air release device.

In some implementations, the pump that is activated to draw fluid out of the air release device is an ultrafiltration pump.

In certain implementations, the method further includes misbalancing a balancing chamber that is in fluid communication with the air release device to draw the fluid out of the air release device.

In some implementations, applying vacuum pressure to the air release device includes closing off lines upstream and downstream of the air release device and activating a pump to draw fluid out of the air release device.

In certain implementations, the dialysis system includes first and second lines connected to the air release device and a pump configured to circulate fluid from the first line to the air release device to the second line during dialysis treatment, and applying vacuum pressure to the air release device includes closing off the second line and operating the pump in a manner to circulate fluid from the second line to the air release device to the first line.

In some implementations, the method further includes indicating to a user that the air release device is not functioning properly if, based on the fluid level within the air release device, it is determined that the air release device is not functioning properly.

In certain implementations, indicating to the user that the air release device is not functioning properly includes emitting a visual signal.

In some implementations, indicating to the user that the air release device is not functioning properly includes emitting an audio signal.

In certain implementations, indicating to the user that the air release device is not functioning properly includes disabling one or more functions of the dialysis system.

In some implementations, the method further includes applying positive pressure to the air release device after applying the vacuum pressure such that air drawn into the air release device by the vacuum pressure is forced out of the air release device by the positive pressure.

In certain implementations, the dialysis system is a hemodialysis system.

In some implementations, the method is performed during hemodialysis treatment.

In certain implementations, the method is performed before hemodialysis treatment.

In some implementations, the fluid within the air release device includes saline.

In certain implementations, the fluid within the air release device includes blood.

In some implementations, the air release device includes a drip chamber and a pressure sensor assembly extending from the drip chamber, and the pressure sensor assembly includes a transducer protector that houses the vent.

In certain implementations, determining whether the air release device is functioning properly includes determining whether the vent of the transducer protector is functioning properly.

In some implementations, detecting the fluid level within the air release device includes detecting a fluid level within the drip chamber.

In certain implementations, the measured pressure is transmitted in the form of a signal to a control unit of the dialysis system.

In some implementations, the control unit is a microprocessor.

In certain implementations, the pressure is measured by a pressure sensor of the dialysis system.

In some implementations, the pressure sensor includes a pressure transducer.

In certain implementations, the pressure sensor is attached to a dialysis machine of the dialysis system and is aligned with the fluid line.

In some implementations, the vacuum pressure is applied to the air release device by activating a pump.

In certain implementations, the line is in fluid communication with a dialyzer, a dialysate line is in fluid communication with the dialyzer, and the pump is an ultrafiltrate pump that is fluidly connected to the dialysate line.

In some implementations, the pump is a drug pump that is configured to introduce fluid into the fluid line when operated in a first direction and is configured to draw fluid out of the fluid line when operated in a second direction.

In certain implementations, applying the vacuum pressure includes operating the drug pump in the second direction.

In some implementations, applying vacuum pressure to the device includes closing off lines upstream and downstream of the device and activating a first pump in fluid communication with a portion of the lines between locations where the lines are closed off.

In certain implementations, closing off the line upstream of the device includes turning off a second pump configured to circulate fluid through the lines, and closing off the line downstream of the air release device includes clamping the line downstream of the device.

In some implementations, the first pump is an ultrafiltration pump.

In certain implementations, the method further includes misbalancing a balancing chamber that is in fluid communication with the device to apply vacuum pressure to the device.

In some implementations, the dialysis system includes first and second lines connected to the device and a pump configured to circulate fluid from the first line to the device to the second line during dialysis treatment, and wherein applying vacuum pressure to the device includes closing off the second line and operating the pump in a manner to circulate fluid from the second line to the device to the first line.

In certain implementations, the device is determined to be functioning improperly if the measured pressure is less than a desired pressure.

In some implementations, the method further includes indicating to a user that the device is not functioning properly if the measured pressure is less than the desired pressure.

In certain implementations, the method further includes applying positive pressure to the device after applying the vacuum pressure such that air drawn into the device by the vacuum pressure is forced out of the device by the positive pressure.

In some implementations, the device includes an air release device.

In certain implementations, the device includes a pressure transducer protector.

Implementations can include one or more of the following advantages.

In some implementations, the device (e.g., the air release device) is tested before treatment begins. As a result, if the device is determined to be functioning improperly, the operator of the system can replace or repair the device prior to treatment such that treatment is not interrupted. Testing the device prior to treatment (e.g., during priming of the dialysis system) also helps to ensure that the operator of the dialysis system is present to promptly replace or repair the device. For example, in many clinical settings, the operator of the dialysis system tends to walk away from the system after the automated portion of the treatment begins. Thus, in such clinical settings, testing the device prior to treatment helps to ensure that the operator of the system is around to correct any identified problem with the device.

In certain implementations, the device (e.g., air release device) is periodically tested during treatment. As a result, damage occurring to the device during treatment can be detected. In the case of an air release device, for example, this technique can be used to detect whether the vent of the air release device has become clogged, which can negatively affect the ability of the vent to vent air or other gases from the air release device to the atmosphere. If the device is determined to be functioning improperly, the operator can quickly take measures to help ensure that treatment is not negatively affected by the malfunctioning device. For example, in implementation in which the device is an air release device of a hemodialysis system, the user can avoid the introduction of additional fluids (e.g., drugs) that might contain air or other gases into the blood circuit, or the user can temporarily stop the treatment and replace or repair the air release device. This can help to ensure that air is not introduced into the patient during treatment.

In some implementations, the testing of the device (e.g., the air release device) is automated. As a result, the operator of the system can identify whether the device is functioning improperly with little effort. This helps to ensure that the operator of the system does not overlook a defective or otherwise malfunctioning device.

In certain implementations, certain functions of the dialysis system are disabled upon determining that the device (e.g., the air release device) is not functioning properly. The disabled functions can, for example, be functions required to perform treatment such that treatment cannot be performed until the malfunctioning device has been repaired or replaced. In some implementations, for example, a pump of the machine can be disabled to prevent the machine from circulating fluid until the device has been replaced or repaired. This helps to ensure that the treatment of the patient is not negatively affected by the malfunctioning device.

Other aspects, features, and advantages will be apparent from the description, drawings, and claims.

DETAILED DESCRIPTION

Figure 1:
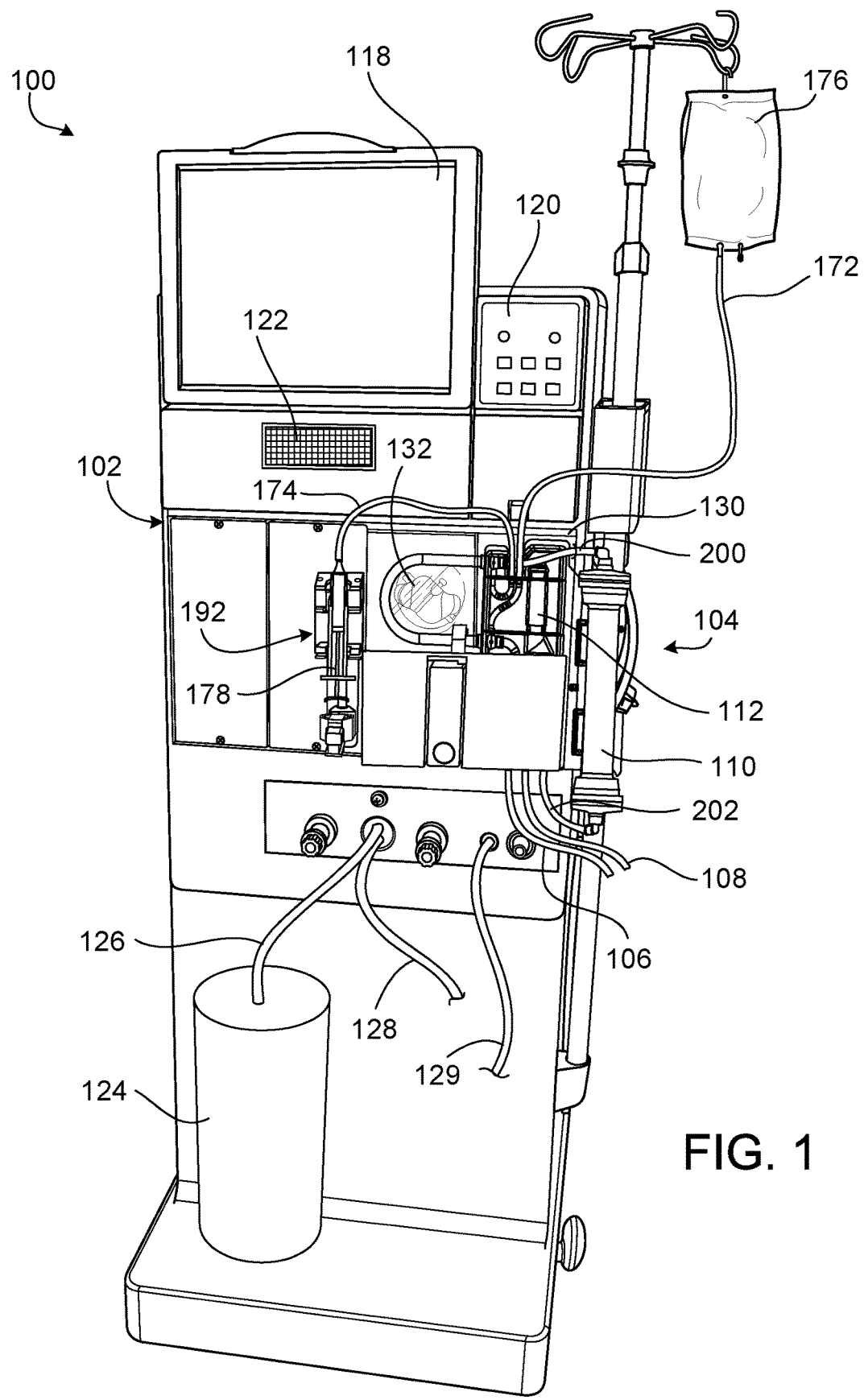
FIG. 1 is a front perspective view of a hemodialysis system.
Figure 2:
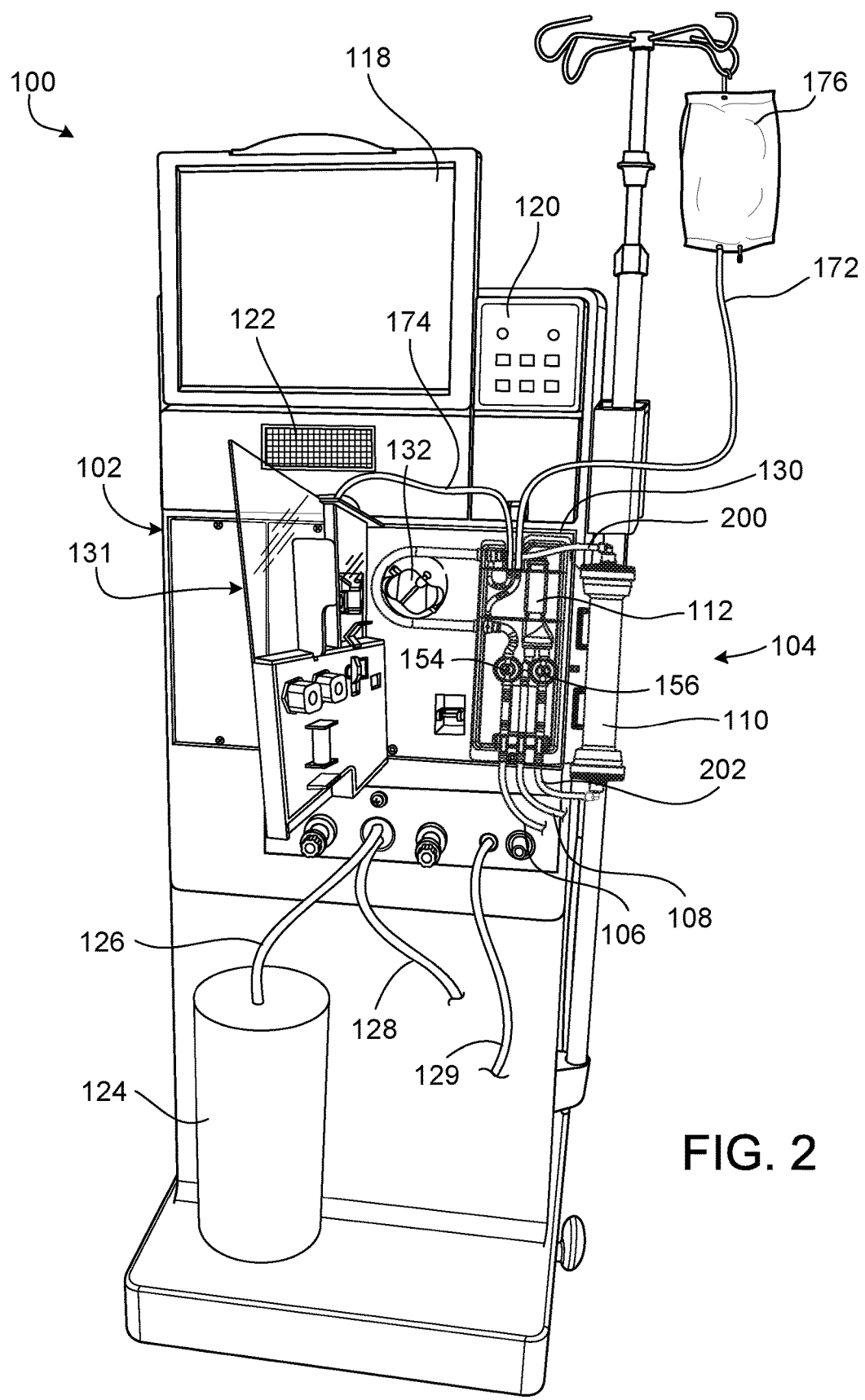
FIG. 2 is a front perspective view of the hemodialysis system of FIG. 1 with a door of a module of the hemodialysis system in an open position to expose a blood component set secured to the module.

Referring to FIGS. 1 and 2, a hemodialysis system 100 includes a hemodialysis machine 102 to which a disposable blood component set 104 that forms a blood circuit is connected. During hemodialysis, arterial and venous patient lines 106, 108 of the blood component set 104 are connected to a patient and blood is circulated through various blood lines and components, including a dialyzer 110, of the blood component set 104. At the same time, dialysate is circulated through a dialysate circuit formed by the dialyzer 110 and various other dialysate components and dialysate lines connected to the hemodialysis machine 102. Many of these dialysate components and dialysate lines are located inside the housing of the hemodialysis machine 102, and are thus not visible in FIGS. 1 and 2. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

Figure 5:
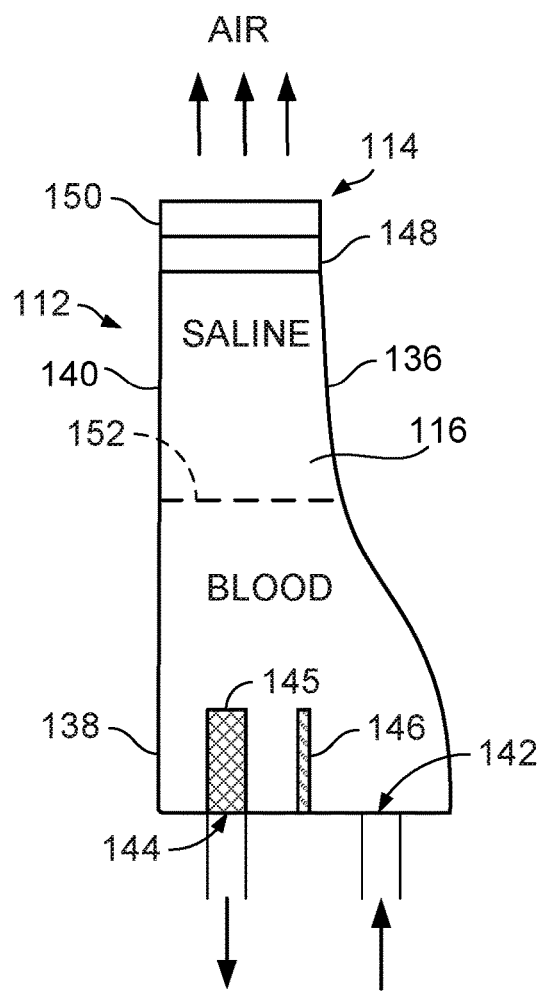
FIG. 5 is a front view of an air release device of the blood component set of FIGS. 3 and 4.
Figure 7:
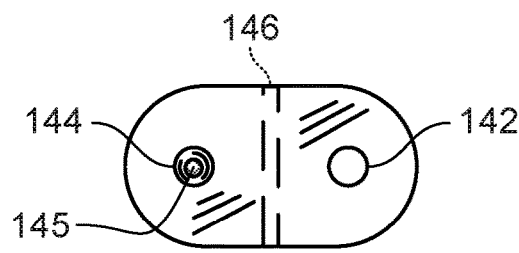
FIG. 7 is a bottom view of the air release device of FIG. 5.
Figure 8:
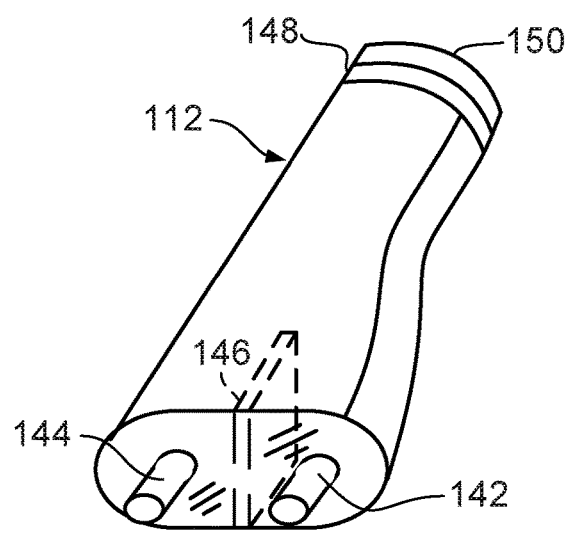
FIG. 8 is a top perspective view of the air release device of FIG. 5, with the air release device lying horizontally on its rear surface.

One of the components of the blood component set 104 is an air release device 112. The air release device 112 includes a self-sealing vent assembly 114 (shown in FIG. 5) that allows air to pass therethrough while inhibiting (e.g., preventing) liquid from passing therethrough. As a result, if blood passing through the blood circuit during treatment contains air, the air will be vented to atmosphere as the blood passes through the air release device 112. The air release device 112 can be tested prior to or during treatment to ensure that it is functioning properly. To test the air release device 112, a vacuum is applied to a chamber 116 (shown in FIG. 5) of the air release device 112 and the liquid level (e.g., saline level or blood level) within the chamber 116 of the air release device 112 and/or the pressure within a portion of the blood circuit including the air release device 112 is monitored. If, in response to the applied vacuum, the liquid level in the chamber 116 of the air release device 112 does not substantially drop and/or the pressure in the portion of the blood circuit including the air release device 112 falls below a certain value, this indicates that an insufficient amount of air is entering the release device 112, which further indicates that the vent assembly 114 of the air release device 112 is likely blocked. In response, the operator can replace or repair the improperly functioning air release device 112 or the entire blood component set 104 of which the air release device 112 is a part. This helps to ensure that any air within the blood circuit during treatment is allowed to escape to atmosphere before reaching the patient. Methods of testing the air release device 112 will be described in greater detail below.

Still referring to FIGS. 1 and 2, the hemodialysis machine 102 includes a touch screen 118 and a control panel 120. The touch screen 118 and the control panel 120 allow the operator to input various different treatment parameters to the hemodialysis machine 102 and to otherwise control the hemodialysis machine 102. In addition, the touch screen 118 serves as a display to convey information to the operator of the hemodialysis system 100. A speaker 122 is positioned below the touch screen 118 and functions to provide audio signals to the operator of the system 100. Thus, the hemodialysis machine 102 is capable of providing both visual alerts via the touch screen 118 and audio alerts via the speaker 122 to the operator of the system 100 during use. While the speaker 122 has been described as being positioned below the touch screen 118, it should be appreciated that the speaker 122 could be positioned at any of various other locations on the hemodialysis machine 102.

As shown in FIGS. 1 and 2, a dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of the spent dialysate and excess fluid drawn from the patient is carried to the drain via the ultrafiltration line 129.

The blood component set 104 is secured to a module 130 attached to the front of the hemodialysis machine 102. The module 130 includes a blood pump 132 capable of driving blood through the blood circuit. The module 130 also includes various other instruments capable of monitoring the blood flowing through the blood circuit. The module 130 includes a door 131 that when closed, as shown in FIG. 1, cooperates with the front face of the module 130 to form a compartment sized and shaped to receive the blood component set 104. In the closed position, the door 131 presses certain blood components of the blood component set 104 against corresponding instruments exposed on the front face of the module 130. As will be described in greater detail below, this arrangement facilitates control of the flow of blood through the blood circuit and monitoring of the blood flowing through the blood circuit.

Figure 3:
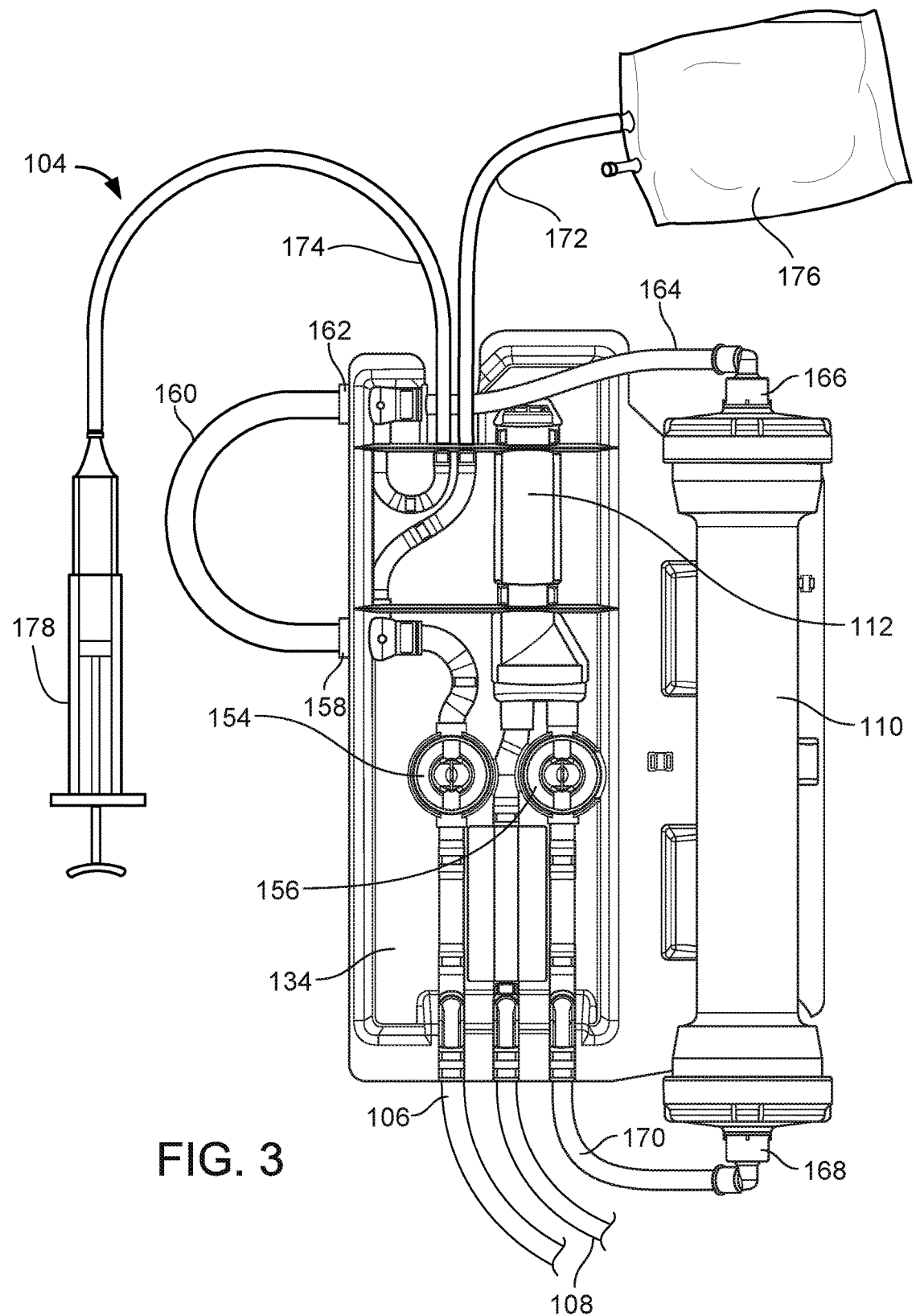
FIG. 3 is a front view of the blood component set of the hemodialysis system of FIGS. 1 and 2.
Figure 4:
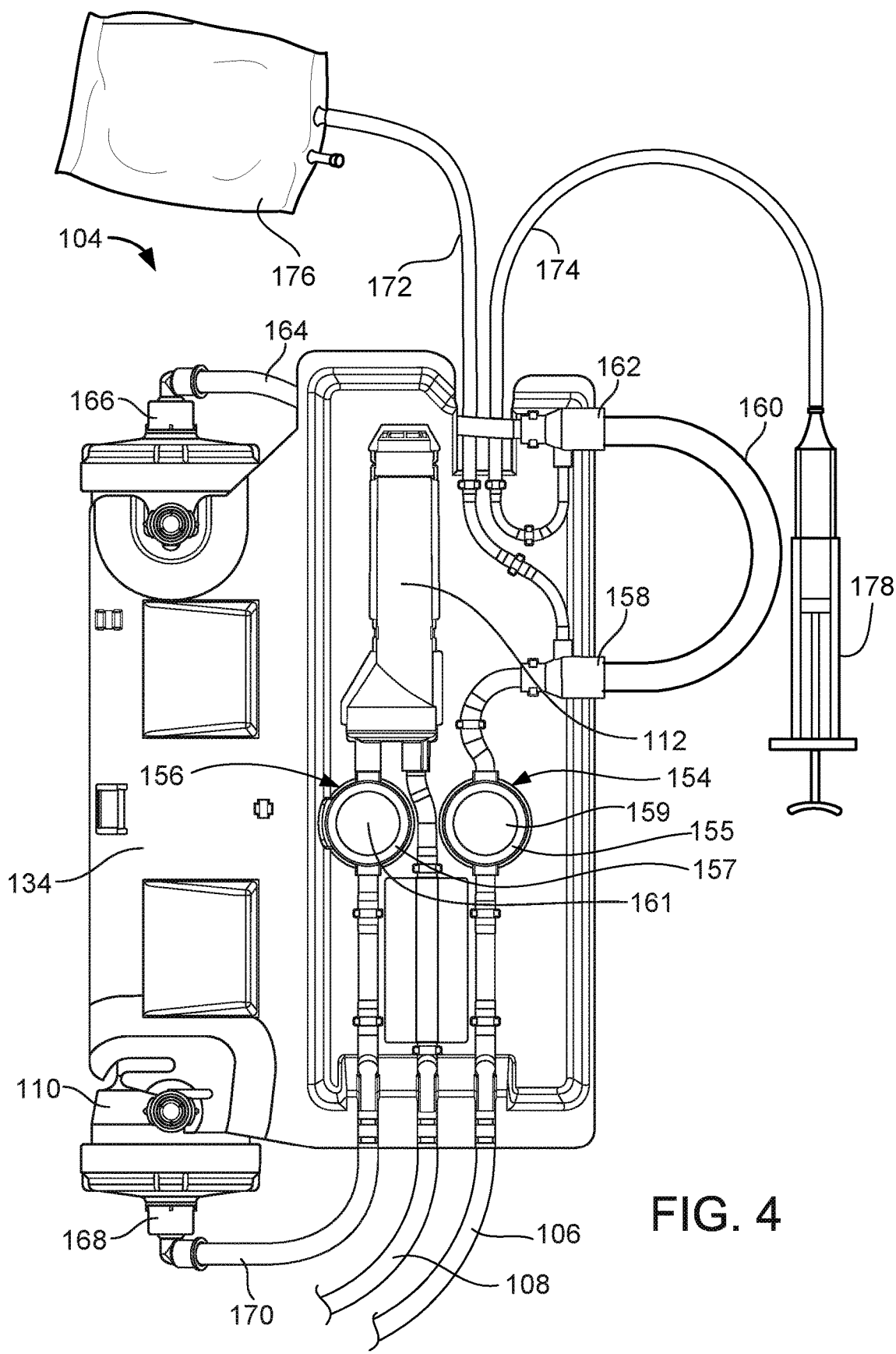
FIG. 4 is a rear view of the blood component set of the hemodialysis system of FIGS. 1 and 2.
Figure 6:
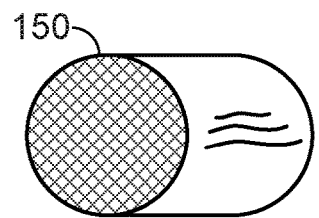
FIG. 6 is a top view of the air release device of FIG. 5.

FIGS. 3 and 4 are front and back views, respectively, of the blood component set 104. As shown in FIGS. 3 and 4, the blood component set 104 includes various different blood lines and blood components, including the air release device 112, that are secured to a carrier body 134. The carrier body 134 forms a series of apertures and recesses for capturing and retaining the various blood lines and components. The carrier body 134 includes a recessed portion (shown on the left side of FIG. 3 and the right side of FIG. 4) and a flat portion (shown on the right side of FIG. 3 and the left side of FIG. 4). The recessed portion is configured to retain most of the blood components while the flat portion is configured to hold the dialyzer 110. As shown in FIG. 4, projections 135 extend from the rear surface of the carrier body 134. These projections 135 cooperate with recessed regions formed in the front face of the module 130 to secure the carrier body 134 and thus the blood component set 104 to the module 130. The projections 135 also help to properly align the blood component set 104 with the front face of the module 130 such that the various blood components and blood lines of the blood component set 104 operatively mate with associated instruments on the front face of the module 130 when the blood component set 104 is secured to the module 130 and the door 131 of the module 130 is closed.

The air release device 112 is retained in an aperture formed in the carrier body 134. The air release device 112 can, for example, be snapped into the aperture formed in the carrier body 134. In some implementations, fingers extending from the carrier body 134 extend part way around the air release device 112 to retain the air release device 112 securely to the carrier body 134. The air release device 112, as noted above, allows gas, such as air, to escape from blood in the blood circuit and out of the chamber 116 of the air release device 112 through the vent assembly 114 positioned at the top of the chamber 116.

Referring to FIGS. 5-8, which illustrate various different views of the air release device 112, the air release device 112 has a housing 136 that forms the air release chamber 116. The chamber 116 has a bottom region 138 and a top region 140. An entry port 142 and an exit port 144 are formed in a bottom surface of the housing 136. A filter 145 is positioned at the exit port 144. The filter 145 inhibits (e.g., prevents) blood clots in the chamber 116 from exiting the air release device 112. A dam 146 extends upward from the bottom surface or floor of the housing between the ports 142, 144 so that all fluid entering the entry port 142 flows over the dam 146 before flowing out the exit port 144.

The self-sealing vent assembly 114 of the air release device 112 is located at the top of the housing 136. The vent assembly 114 is designed to permit air to escape from the chamber 116 while inhibiting (e.g., preventing) liquid from escaping from the chamber 116. The vent assembly 114 includes a micro-porous membrane 148 and a vent structure 150. The micro-porous membrane 148 allows gas (e.g., from air bubbles in the blood or other circulating liquids) to vent from the chamber 116 to the atmosphere. At the same time, pores in the micro-porous membrane 148 are small enough to keep foreign particles and organisms from entering the chamber 116 from the outside air. In some implementations, the membrane 148 includes a hydrophobic material, such as polytetrafluoroethylene (PTFE) (e.g., expanded polytetrafluoroethylene (ePTFE)). In certain implementations, the membrane 148 is a fibrous carrier with a matted and woven layer on top of which ePTFE or other micro-porous material is applied. The hydrophobic micro-porous membrane 148 keeps liquid from leaking out of the chamber 116 when the chamber 116 is substantially filled with liquid and allows air to pass therethrough. The membrane 148 has an average pore size of about 0.05 microns to about 0.45 microns (e.g., about 0.22 microns, about 0.2 microns). Suitable membranes are available from Pall Corporation, East Hills, N.Y., under the Versapor® mark and from W. L. Gore & Associates, Inc., Newark, Del.

The vent structure 150 automatically seals shut if it gets wet. As a result, the vent structure 150 can prevent blood from escaping from the chamber 116 or other liquids from entering the chamber 116 in the event of the membrane 148 rupturing. In some implementations, the vent structure 150 is a solid porous block, having an average pore size of about 15 micron to about 45 microns, that allows air to pass through and escape from the chamber. In certain implementations, the vent structure 150 is formed of a blend of polyethylene (e.g., high density polyethylene (HDPE)) and carboxymethylcellulose (CMC), a blend of polystyrene and methyl-ethyl-cellulose or of polypropylene- or polyethylene-based porous material. Such materials are available from Porex Corporation, Fairburn, Ga. One such product contains 90% by weight polyethylene and -10% by weight carboxymethylcellulose with an average pore size of about 30 microns to about 40 microns. However, other percentages of the materials can be used, as well as other materials and other pore sizes. For example, the vent structure 150 can include about 80% to about 95% by weight high density polyethylene and about 5% to about 20% by weight carboxymethylcellulose.

When the vent structure 150 comes into contact with liquid, the swelling agent (e.g., cellulose component, such as carboxymethylcellulose) of the vent structure expands, thereby closing off the pores in the polymer component (e.g., high density polyethylene) of the vent structure 150. The vent structure 150 is mounted adjacent to and just above the membrane 148 so that the membrane 148 is located between the vent structure 150 and the chamber 116. The vent structure 150 inhibits (e.g., prevents) condensation from accumulating on and contacting the membrane 148. For example, if condensation begins to build up on the vent structure 150, the pores of the vent structure close thereby inhibiting the condensation from reaching the membrane 148. The vent structure 150 similarly inhibits (e.g., prevents) liquid from escaping from the chamber 116. If, for example, the membrane 148 were to rupture and liquid were to pass through the ruptured membrane 148, the pores of the vent structure 150 would automatically close upon coming into contact with the liquid.

When the chamber 116 of the air release device 112 contains blood, inhibiting (e.g., preventing) the protein in the blood from accumulating on the membrane 148 can maintain the hydrophobic characteristic of the membrane 148. Whole blood can be kept from the membrane 148 by providing saline between the blood and the membrane 148. The height and shape of the chamber 116 are sufficient to maintain a blood/saline interface 152, and thus inhibits (e.g., prevents) the saline above the interface 152 from substantially mixing with blood below the interface 152.

Suitable air release devices are described in greater detail in U.S. patent application Publication No. 2009/0071911, entitled "Safety Vent Structure for Extracorporeal Circuit," which is incorporated by reference herein.

Referring back to FIGS. 3 and 4, arterial and venous pressure sensor capsules 154, 156 are also positioned in apertures formed in the carrier body 134 of the blood component set 104. Each of the pressure sensor capsules 154, 156, as shown in FIG. 4, includes an annular rigid member 155, 157 to which a thin membrane 159, 161 is secured. The annular rigid members 155, 157 and the thin membranes 159, 161 of the capsules 154, 156 together form a pressure sensor chamber through which blood flows during use. When the blood component set 104 is secured to the front face of the module 130 of the hemodialysis machine 102, the thin membranes 159, 161 of the pressure sensor capsules 154, 156 face the front face of the module 130. The pressure within the pressure sensor chambers can be detected through the thin membranes 159, 161 by pressure sensors (e.g., a pressure transducers) on the front face of the module 130 during use. Suitable capsules are described further in U.S. Pat. No. 5,614,677, "Diaphragm Gage for Measuring the Pressure of a Fluid," which is incorporated herein by reference.

The arterial patient line 106, as shown in FIGS. 3 and 4, is contained within a recess formed in the carrier body 134. One end of the arterial patient line 106 is fluidly connected to an artery of a patient during treatment. The arterial patient line 106 is also fluidly connected to the pressure sensor capsule 154. The arterial patient line 106 extends along the recess to a first pump line adaptor 158, which connects the arterial patient line 106 to one end of a U-shaped pump line 160. The other end of the pump line 160 is connected to a second pump line adaptor 162, which is fluidly connected to a dialyzer inlet line 164. The dialyzer inlet line 164 is connected via a tube adaptor to a blood entry port 166 of the dialyzer 110. A blood exit port 168 of the dialyzer 110 is connected to another tube adaptor, which connects the dialyzer 110 to a dialyzer outlet line 170. The pressure sensor capsule 156 is positioned along the dialyzer outlet line 170, upstream of the air release device 112. The pressure sensor capsule 156 is fluidly connected to the entry port 142 (shown in FIG. 5) of the air release device 112. The pressure sensor capsule 156 allows blood pressure on the venous side of the dialyzer 110 to be sensed by a mating pressure sensor on the front face of the module 130 during treatment. The venous patient line 108 is connected to the exit port 144 (shown in FIG. 5) of the air release device 112. The venous patient line 108 extends from the air release device 112 and is fluidly connected to a vein of a patient during treatment.

Still referring to FIGS. 3 and 4, in addition to the blood lines forming the main blood circuit described above, a saline delivery line 172 and a drug delivery line 174 are connected to the blood circuit for introducing saline and drugs (e.g., heparin) into the blood circuit. The saline delivery line 172 is connected to a saline bag 176. The drug delivery line 174 is connected to a syringe 178 that contains a drug. The saline delivery line 172 is connected to the first pump line adaptor 158, and the drug delivery line 174 is connected to the second pump line adaptor 162.

The various blood lines, the saline delivery line 172, and the drug delivery line 174 can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate. In some implementations, the blood component carrier body 134 is formed of PVC, polyethylene, polypropylene, polystyrene, and/or high density polyethylene. The various blood lines, the saline delivery line 172, and the drug delivery line 174 are typically retained within recessed channels formed in the carrier body 134. The recessed channels can have a diameter equal to or slightly less than the diameters of the lines so that the lines are retained within the channels with a friction fit. Alternatively or additionally, any of various other techniques can be used to secure the lines to the carrier body 134. For example, mechanical attachment devices (e.g., clips or clamps) can be attached to the carrier body 134 and used to retain the lines. As another example, the lines can be adhered to or thermally bonded to the carrier body 134.

Suitable blood component sets and their related components are described in greater detail in U.S. Patent Application Publication No. 2009/0101566, entitled "Dialysis Systems and Related Components," which is incorporated by reference herein.

Figure 9:
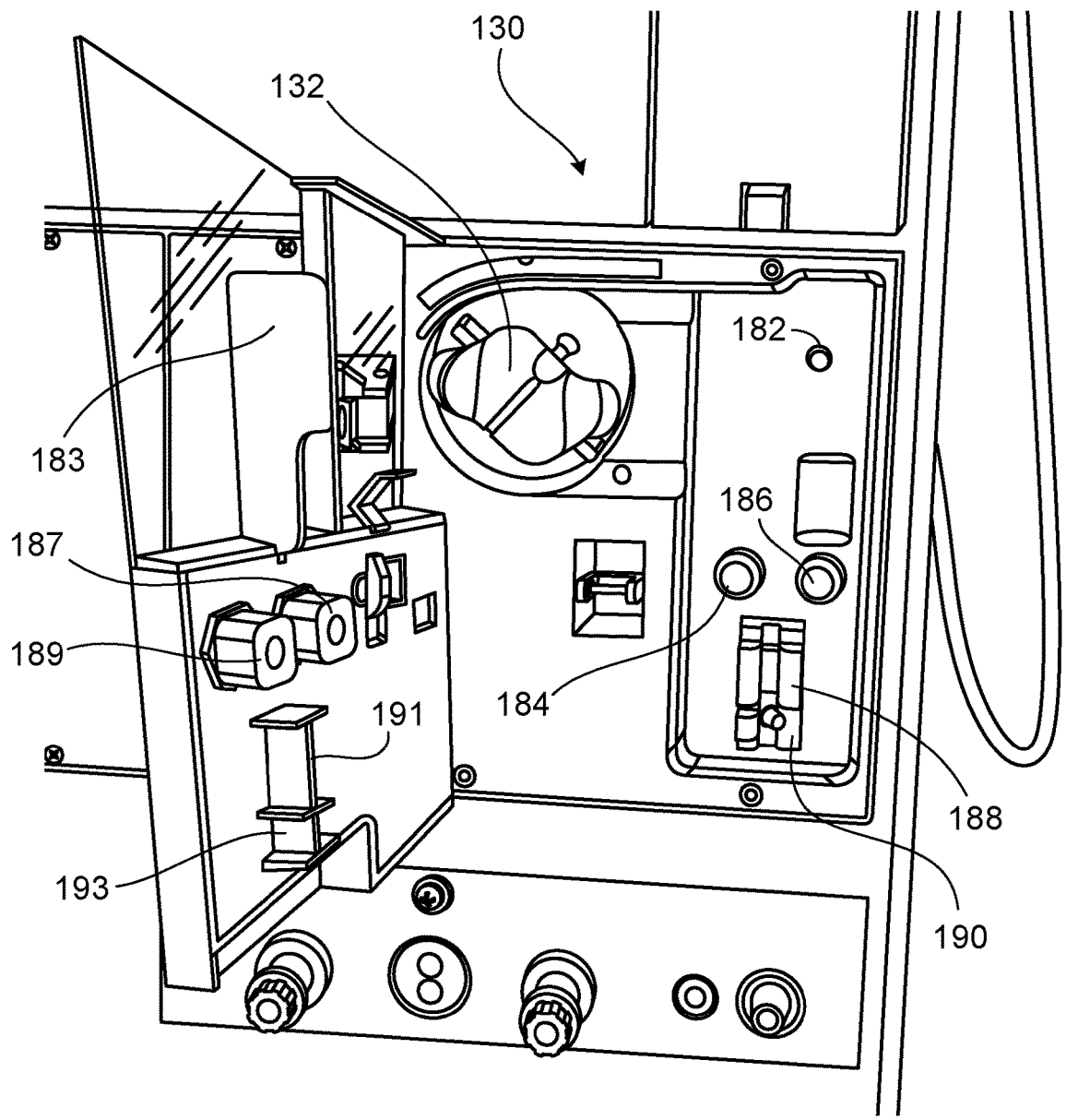
FIG. 9 is a front view of the hemodialysis system of FIG. 1 with the door of the module of the system in an open position and the blood component set removed from the module to expose blood pumping and monitoring instruments on the front face of the module.

FIG. 9 is an enlarged front view of the module 130 of the hemodialysis machine 102 with the door 131 of the module 130 open and the blood component set 104 removed from the module 130. As shown in FIG. 9, the blood pump 132 extends from the front face of the module 130 of the hemodialysis machine 102. The blood pump 132 is a peristaltic pump and is arranged so that the U-shaped pump line 160 extending laterally from the carrier body is positioned around the peristaltic pump when the blood component set 104 is secured to the front face of the module 130.

The module 130 of the hemodialysis machine 102 also includes a level detector 182 that aligns with the air release device 112 when the blood component set 104 is secured to the front face of the module 130. The level detector 182 is adapted to detect the level of liquid (e.g., blood and/or saline) within the air release device 112. The door 131 of the module 130 includes a projection 183 that compresses the air release device 112 against the level detector 182 when the blood component set 104 is secured to the front face of the module 130 and the door 131 is closed. The projection 183 includes a recessed region adapted to receive the rounded exterior surface of the air release device 112. The recessed region helps to ensure that the air release device 112 is properly positioned with respect to the level detector 182 when the door 131 is closed. The level detector 182 is a cylindrical member having a relatively soft tip (e.g., a sponge tip) that contacts the outer surface of the air release device 112 when the door 131 presses the air release device 112 against the level detector 182. The tip of the level detector 182 includes an ultrasound signal transmitter and receiver for determining the level of liquid in the air release device 112. During use, the transmitter emits an ultrasonic signal that reflects off of the contents in the air release chamber 112. The reflected signal is then detected by the receiver. The reflected signal can be used to determine the contents in the air release chamber 116 at the level of the level detector 182. The receiver can, for example, be adapted to distinguish between liquid, air, and a combination of liquid and air (e.g., foam). As a result, the level detector 182 can detect when the blood level within the chamber 116 drops due to the entry of air into the chamber 116.

While the tip of the level detector 182 has been described as including a separate transmitter and receiver, in some implementations, the level detector includes a transmitter/receiver that performs both functions of transmitting and receiving.

Still referring to FIG. 9, the module 130 of the hemodialysis machine 102 also includes arterial and venous pressure transducers 184, 186 that align with the pressure sensor capsules 154, 156 of the blood component set 104 when the blood component set 104 is secured to the front face of the module 130 and the door 131 of the module 130 is closed. The pressure transducers 184, 186 are capable of measuring the pressure of blood flowing through the capsules 154, 156. The pressure transducers 184, 186 are cylindrical members having substantially flat surfaces exposed on the front face of the module 130. The door 131 includes spring-loaded plungers 187, 189 that compress the annular rigid members 155, 157 (shown in FIG. 4) of the pressure sensor capsules 154, 156 between the door 131 and the front face of the module 130 when the blood component set 104 is secured to the front face of the module 130 and the door 131 is closed. As a result, the membranes 159, 161 (shown in FIG. 4) of the pressure sensor capsules 154, 156 are pressed against the pressure transducers 184, 186 and a seal is created between the perimeter of each of the thin membranes 159, 161 and the front face of the module 130. The central regions of the membranes 159, 161 of the pressure sensor capsules 154, 156 contact the flat surfaces of the pressure transducers 184, 186. As the fluid pressure changes within the pressure sensor capsules 154, 156, the amount of pressure applied to the pressure transducers 184, 186 by the pressure sensor capsules 154, 156 also changes. The pressure transducers 184, 186 are capable of detecting these pressure changes during use.

An air bubble detector 188 also extends from the front face of the module 130. When the blood component set 104 is secured to the front face of the module 130, the venous patient line 108 passes through (e.g., is threaded through) the air bubble detector 188. The air bubble detector 188 includes a housing that forms a channel in which the venous patient line 108 is received. The door 131 of the module 130 includes a fin 191 that presses the venous patient line 108 into the channel of the housing and against a sensor of the air bubble detector 188 when the door 131 is closed. The air bubble detector 188 is capable of detecting air bubbles within the venous patient line 108. In some implementations, the air bubble detector 188 is an optical detector. The OPB 350 bubble detector made by Optek can, for example, be used. Any of various other types of optical detectors can alternatively or additionally be used. Similarly, other types of sensors, such as sensors utilizing ultrasound technology can be used as the air bubble detectors.

Downstream of the air bubble detector 188, the venous patient line 108 passes through (e.g., is threaded through) an occluder or clamp 190. Similar to the air bubble detector 188, the occluder 190 has a housing that forms a channel in which the venous patient line 108 is received. The door 131 of the module 130 includes a fin 193 that presses the venous patient line 108 into the channel of the housing of the occluder 190 when the door 131 is closed. The occluder 190 is configured to crimp the portion of the venous patient line 108 disposed therein to prevent blood from passing through the venous patient line 108 when activated. The occluder 190 can, for example, be connected to the air bubble detector 188 so that the occluder 190 can be activated when the air bubble detector 188 detects an air bubble within the venous patient line 108. Such an arrangement helps to ensure that no air bubbles reach the patient in the event that the air release device 112 fails to remove one or more air bubbles from the blood. In some implementations, the occluder 190 is a solenoid based ram. Alternatively or additionally, other types of automated occluders can be used.

Referring briefly to FIG. 1, a drug pump 192 also extends from the front of the hemodialysis machine 102. The drug pump 192 is a syringe pump that includes a clamping mechanism configured to retain the syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via the drug delivery line 174 during use, or to draw liquid from the blood circuit into the syringe 178 via the drug delivery line 174 during use.

As discussed in more detail below, as an alternative to or in addition to using a drug-containing syringe in combination with a syringe pump to inject liquid drug into the blood circuit or to draw liquid our of the blood circuit, the system can be adapted to pump liquid drug into the blood circuit from a drug vial and/or to draw liquid out of the blood circuit and into a vial.

The level detector 182, the pressure transducers 184, 186, the touch screen 118, and the speaker 122 are connected to a control unit (e.g., a microprocessor) of the hemodialysis machine 102. These devices can be connected to the microprocessor in any manner that permits signals to be transmitted from the devices to the microprocessor and vice versa. In some implementations, electrical wiring is used to connect the microprocessor to the instruments. Wireless connections can alternatively or additionally be used. As described below, the microprocessor can activate an audio and visual alarm using the speaker 122 and the touch screen 118 upon receiving signals indicating that the liquid level detected by the level detector 182 is outside a desired liquid level range and/or upon receiving signals that the pressure sensed by the pressure transducer 186 is outside a desired pressure range. Liquid levels and pressures detected to be outside of a desired range, as discussed in greater detail below, can indicate that the air release device 112 (e.g., the vent assembly 114 of the air release device 112) is not functioning properly.

Still referring to FIG. 1, the dialysate circuit is formed by multiple dialysate components and dialysate lines positioned inside the housing of the hemodialysis machine 102 as well as the dialyzer 110, a dialyzer inlet line 200, and a dialyzer outlet line 202 that are positioned outside of the housing of the hemodialysis machine 102. The dialyzer inlet line 200 includes a connector adapted to connect to one end region of the dialyzer 110, and the dialyzer outlet line 202 includes a connector adapted to connect to another end region of the dialyzer 110.

Figure 10:
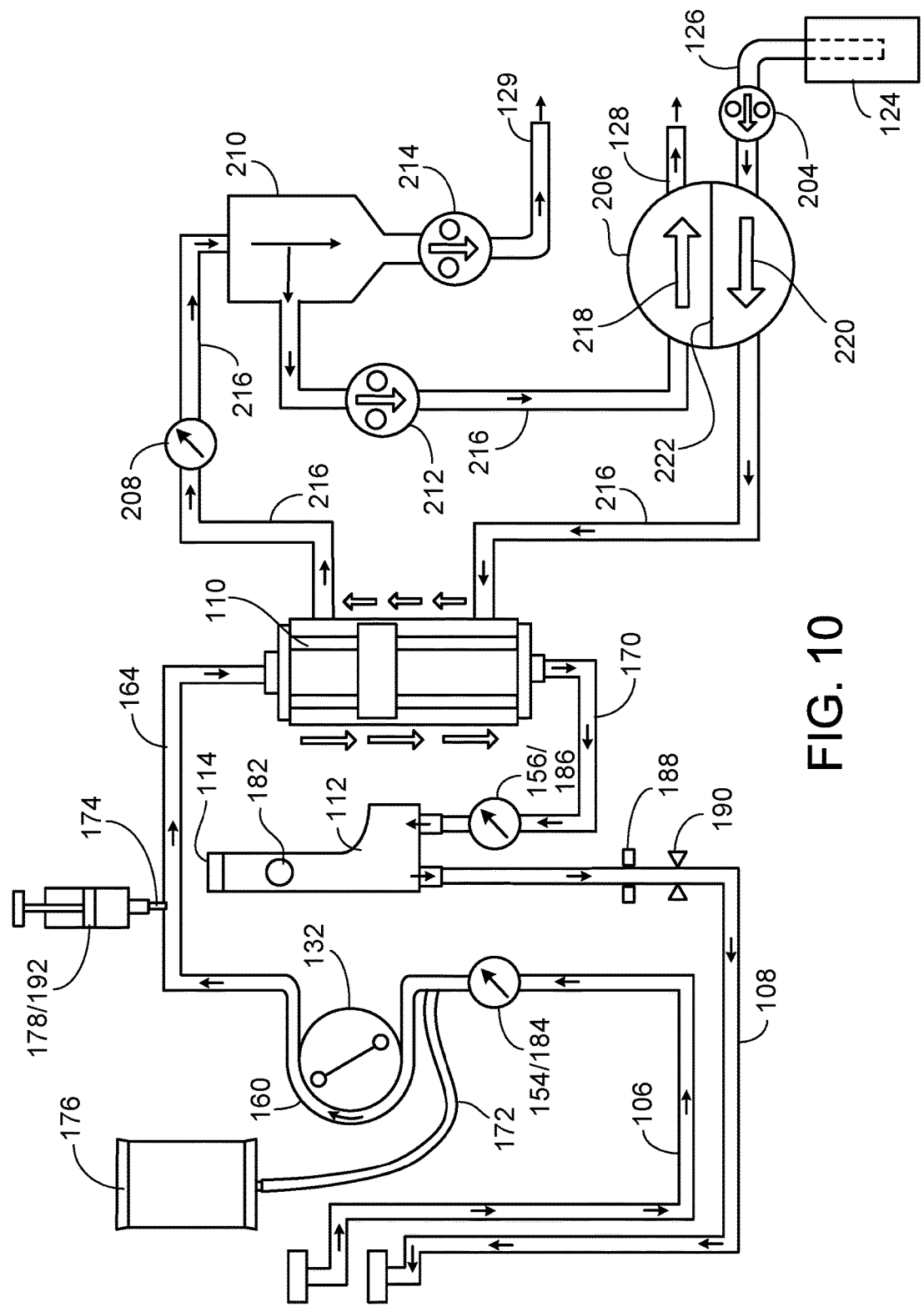
FIG. 10 is a schematic of fluid flow through the blood circuit and dialysate circuit of the hemodialysis system of FIG. 1.

FIG. 10 is a schematic showing the flow paths of fluids into, through, and out of the blood circuit and the dialysate circuit of the hemodialysis system 100. Referring to the right side of FIG. 10, the dialysate components of the dialysate circuit that are located inside the housing of the hemodialysis machine 102 include a first dialysate pump 204, a balancing device 206, a pressure sensor 208, an equalizing chamber 210, a second dialysate pump 212, and an ultrafiltration pump 214. These dialysate components are fluidly connected to one another via a series of dialysate lines 216.

The dialysate pump 204 is capable of pumping dialysate to the balancing chamber 206 via the dialysate supply line 126. In some implementations, the dialysate pump 204 is a peristaltic pump. However, any various other types of pumps can alternatively or additionally be used. Examples of other suitable types of pumps include diaphragm pumps and gear pumps.

The balancing device 206 includes a spherical chamber that is divided into a first chamber half 218 and a second chamber half 220 by a flexible membrane 222. As fluid flows into the first chamber half 218, fluid is forced out of the second chamber half 220, and vice versa. This balancing device construction helps to ensure that the volume of fluid entering the balancing device 206 is equal to the volume of fluid exiting the balancing device 206. This helps to ensure that the volume of fresh dialysate entering the dialysate circuit is equal to the volume of spent dialysate exiting the dialysate circuit when desired during treatment, as described in greater detail below.

During hemodialysis, the dialysate exiting the second chamber half 220 is directed through the dialyzer 110 toward the equalizing chamber 210. The pressure sensor 208 located along the dialysate line 216 connecting the dialyzer 110 to the equalizing chamber 210 is adapted to measure the pressure of the spent dialysate exiting the dialyzer 110. Any of various different types of pressure sensors capable of measuring the pressure of the spent dialysate passing from the dialyzer 110 to the equalizing chamber 210 can be used.

The spent dialysate collects in the equalizing chamber 210. The dialysate pump 212 is configured to pump the spent dialysate from the equalizing chamber 210 to the first chamber half 218 of the balancing device 206. In some implementations, the dialysate pump 212 is a peristaltic pump. However, any various other types of pumps can alternatively or additionally be used. Examples of other suitable types of pumps include diaphragm pumps and gear pumps. As the first chamber half 218 of the balancing device 206 fills with the spent dialysate, fresh dialysate within the second chamber half 220 is expelled toward dialyzer 110. Subsequently, as the second chamber half 220 is refilled with fresh dialysate, the spent dialysate within the first chamber half 218 is forced through the drain line 128 to the drain.

The ultrafiltration line 129 is connected to an outlet of the equalizing chamber 210. The ultrafiltration pump 214 is operatively connected to the ultrafiltration line 129 such that when the ultrafiltration pump 214 is operated, spent dialysate can be pulled from the equalizing chamber 210 and directed to the drain via the ultrafiltration line 129. Operation of the ultrafiltration pump 214 while simultaneously operating the dialysate pump 212 causes increased vacuum pressure within the dialysate line 216 connecting the equalizing chamber 210 to the dialyzer 110, and thus creates increased vacuum pressure within the dialyzer 110. As a result of this increased vacuum pressure, additional fluid is pulled from the blood circuit into the dialysate circuit across the semi-permeable structure (e.g., semi-permeable membrane or semi-permeable microtubes) of the dialyzer 110. In certain implementations, the ultrafiltration pump 214 is a peristaltic pump. However, any various other types of pumps can alternatively or additionally be used. Examples of other suitable types of pumps include diaphragm pumps and gear pumps.

Referring to FIGS. 1 and 10, a method of preparing the hemodialysis system 100 for hemodialysis treatment will now be described. Before hemodialysis treatment is initiated, saline is introduced from the saline bag 176 into the blood circuit via the saline delivery line 172 in order to prime the blood circuit. To draw the saline from the saline bag 176 into the blood circuit, a valve along the saline delivery line 172 is opened, a valve along the dialysate supply line 126 is closed, and the blood pump 132 is turned on. The saline enters the blood circuit via the pump line adaptor 158 (shown in FIGS. 3 and 4) and then flows through the U-shaped blood line 160 that engages the blood pump 132. The blood pump 132 forces the saline through the blood circuit toward the dialyzer 110. The saline flows through the dialyzer 110 and exits the dialyzer 110 via the dialyzer outlet line 170. As the saline flows through the dialyzer outlet line 170 toward the air release device 112, the saline passes through the venous pressure sensor capsule 156. Next, the saline flows through the entry port 142 of the air release device 112 and fills the chamber 116 of the air release device 112. To fill the chamber 116 completely, the venous patient line 108, which leads away from the air release device 112, is clamped while the saline is forced into the chamber 116. If the vent assembly 114 of the air release device 112 is functioning properly, air is forced out the top of the chamber 116 and through the vent assembly 114 as saline fills the chamber 116. The saline does not pass through the vent assembly 114 if the vent assembly 114 is functioning properly because the membrane 148 of the vent assembly 114 is hydrophobic.

If the vent assembly 114 of the air release device 112 is not functioning properly, air within the blood circuit may not be allowed to escape from the chamber 116 of the air release device 112 during use. Such an improperly functioning air release device 112 might not be noticed during the priming procedure. For example, if a relatively small volume of air is within the blood circuit when the priming occurs, that small volume of air, which would get trapped in the chamber 116 of the air release device 112, might go unnoticed by the operator of the hemodialysis system 100. Therefore, it is advantageous to test the operability of the air release device 112 after priming and before treatment.

In order to test the air release device 112, the blood pump 132 is turned off, the venous patient line 108 is clamped, and the ultrafiltration pump 214 is started. Because the blood pump 132 is turned off, the blood pump 132 acts as a closed clamp on the arterial patient line 106. Therefore, the blood circuit acts as a substantially closed fluid circuit with the vent assembly 114 of the air release device 112 being the only point of entry and exit for air or other gases. The vacuum pressure created across the semi-permeable structure of the dialyzer 110 by running the ultrafiltration pump 214 causes saline to be pulled from the blood circuit to the dialysate circuit. Because the arterial and venous patient lines 106, 108 are clamped, the only fluid access to the blood circuit is through the vent assembly 114 of the air release device 112. Therefore, if the vent assembly 114 of the air release device 112 is functioning properly, air will be pulled across the vent assembly 114 and into the chamber 116 of the air release device 112 due to the vacuum pressure. The ultrafiltration pump 214 continues to run until a sufficient vacuum is applied to the dialysate circuit to draw enough air into the air release device 112 (assuming a properly functioning air release device 112) to activate the level detector 182. In other words, the ultrafiltration pump 214 continues to run until a sufficient amount of air would be pulled through the vent assembly 114 of a properly functioning air release device 112 to cause the saline level within the air release device 112 to drop below the level of the level detector 182. Typically, the ultrafiltration pump 214 is operated in a manner to draw a sufficient amount of air into a properly functioning air release device to activate the level detector 182 without drawing so much air into the blood circuit that the air reaches the venous patient line 108 causing the air bubble detector 188 and occluder 190 to be activated.

Various different parameters affect the volume of air pulled into the chamber 116 of a properly functioning air release device 112. For example, the operation time of the ultrafiltration pump 214, the pump speed of the ultrafiltration pump 214, the permeability of the vent assembly 114 of the air release device 112, etc. dictate the volume of air pulled into the air release device 112. In some implementations, the ultrafiltration pump 214 is operated for about ten seconds to about one minute (e.g., about 30 seconds) during the test procedure. In certain implementations, the ultrafiltration pump is operated to pump fluid at a rate of about 1 L/hr to about 4 L/hr (e.g., about 2 L/hr to about 3 L/hr).

As air is drawn into the chamber 116 of the air release device 112, the liquid level within the chamber 116 drops. When the liquid level drops below the level at which the level detector 182 is positioned, the level detector 182 will no longer detect liquid in the chamber 116 of the air release device 112. As a result, the level detector 182 will transmit a signal to the microprocessor, indicating the absence of liquid in the air release device 112 at the height of the level detector 182. If the level detector 182 detects the absence of liquid in the chamber 116 of the air release device 112 after running the ultrafiltration pump 214 for the desired time and at the desired speed, this indicates that the air release device 112 is functioning properly. If, however, the level detector 182 still detects liquid in the chamber 116 of the air release device 112 after running the ultrafiltration pump 214 for the desired time and at the desired speed, this indicates that the air release device 112 is not functioning properly. The microprocessor of the hemodialysis machine 102 is configured to activate a visual and audio alarm upon receiving signals from the level detector 182 that the liquid level within the chamber 116 has not dropped below the level of the level detector 182 after operating the ultrafiltration pump 214 for the desired time and at the desired speed. In particular, the microprocessor transmit signals to the touch screen 118 and the speaker 122, causing the touch screen 118 to emit a visual signal and the speaker 122 to emit an audio signal. These visual and audio signals alert the operator of the system 100 to the possibility of a malfunctioning air release device 112 (e.g., a malfunctioning vent structure 114 of the air release device 112).

After determining whether the air release device 112 is functioning properly, any air that was drawn into the air release device 112 is forced back out to the atmosphere. To do this, the ultrafiltration pump 214 is turned off and the blood pump 132 is turned on. Because the venous patient line 108 is still clamped at this time, the operation of the blood pump 132 builds a substantial amount of pressure within the blood circuit. This pressure forces the air within the chamber 116 of the air release device 112 to exit the chamber 116 via the vent assembly 114 of the air release device 112.

If it was determined that the air release device 112 was not functioning properly during the test procedure, then the air release device 112 can be replaced or repaired. In some implementations, for example, the operator may simply disconnect all of the blood lines and blood components of the blood component set 104 and discard that entire blood component set 104. A new blood component set 104 would then be connected to the hemodialysis machine 102. Alternatively, the air release device 112 alone could be disconnected from the carrier body 134 of the blood component set 104 and replaced with a new air release device 112. As another alternative, the vent assembly 114 of the malfunctioning air release device 112 could be removed from the air release device 112 and replaced with a new vent assembly 114. The air release device 112 with the new vent assembly 114 would then be reconnected to the remainder of the blood component set 104. After replacing or repairing the air release device 112, the priming and testing processes described above would be repeated prior to beginning hemodialysis treatment.

In some implementations, the microprocessor of the hemodialysis machine 102 is adapted to disable certain functions of the hemodialysis machine 102 until the operator of the system 100 indicates that the malfunctioning air release device 112 has been replaced or repaired or until the hemodialysis machine 102 itself is able to confirm that the malfunctioning air release device 112 has been replaced or repaired (e.g., by detecting an acceptable level of liquid within the chamber 116 of the air release device 112 during a subsequent test). The functions that are disabled by the microprocessor can, for example, be functions required to carry out hemodialysis treatment. Disabling these features can help to ensure that treatment is not performed using a blood component set with a malfunctioning air release device.

Figure 11:
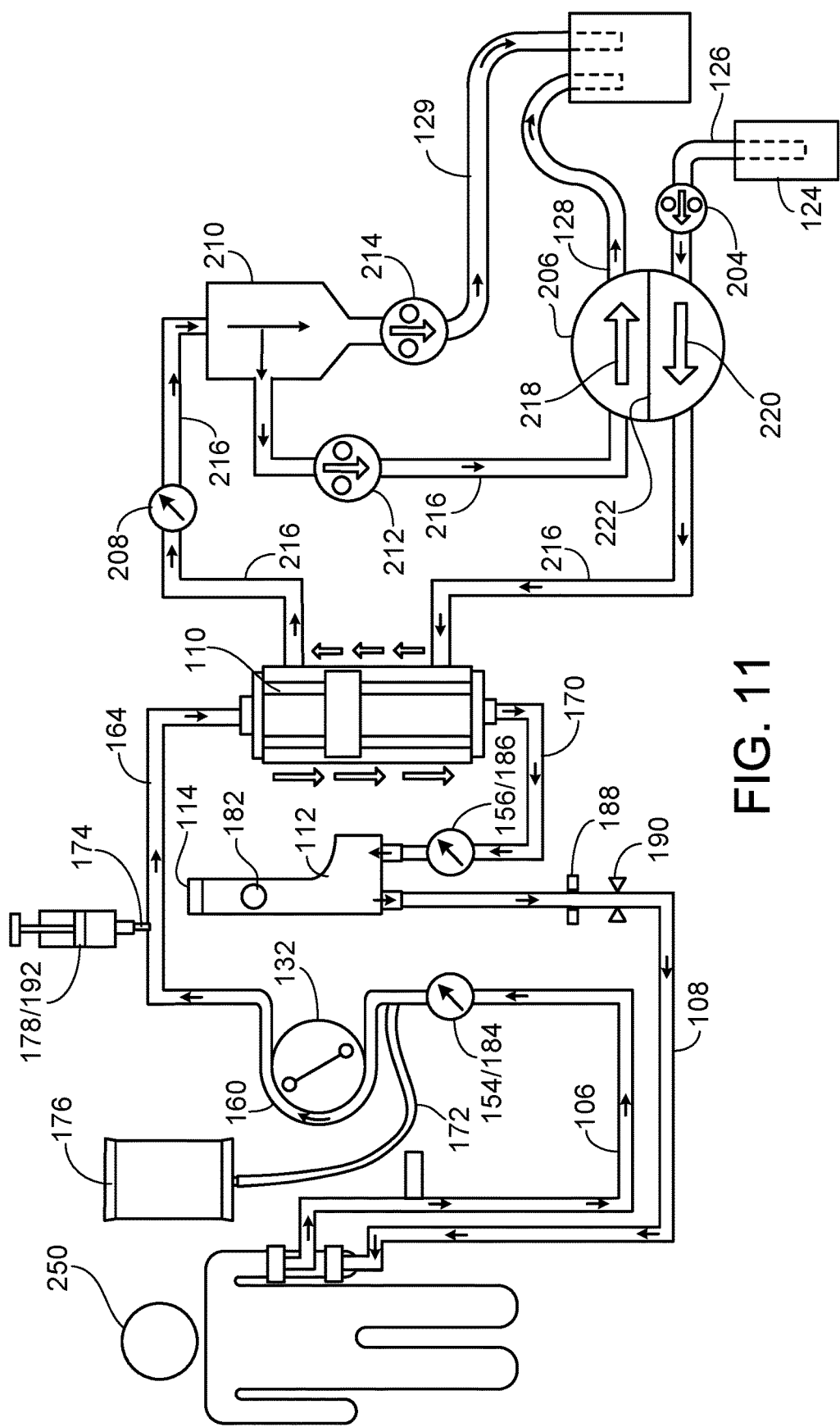
FIG. 11 is a schematic of fluid flow through the blood circuit and dialysate circuit of the hemodialysis system of FIG. 1 when the hemodialysis system is connected to a patient for treatment.

After priming the blood circuit and confirming that the air release device 112 is functioning properly, the arterial and venous patient lines 106, 108 are connected to a patient 250, as shown in FIG. 11, and hemodialysis is initiated. During hemodialysis, blood is circulated through the blood circuit (i.e., the various blood lines and blood components, including the dialyzer 110, of the blood component set 104). At the same time, dialysate is circulated through the dialysate circuit (i.e., the various dialysate lines and dialysate components, including the dialyzer 110).

Focusing first on the blood circuit shown on the left side of FIG. 11, during hemodialysis, the blood pump 132 is activated causing blood to circulate through the blood circuit. The blood follows the same basic route as the route of the saline described above and, for the most part, pushes the residual saline in the blood circuit through the various blood components and blood lines and back to the patient. The blood is drawn from the patient 250 via the arterial patient line 106 and flows to the arterial pressure sensor capsule 154. The arterial pressure sensor 184 on the front face of the module 130 (shown in FIG. 9) aligns with the pressure sensor capsule 154 and measures the pressure of the blood flowing through the blood circuit on the arterial side. The blood then flows through the U-shaped pump line 160, which is operatively engaged with the blood pump 132. From the pump line 160, the blood flows to the dialyzer 110. After exiting the dialyzer 110, the blood flows through the venous pressure sensor capsule 156 where the pressure of the blood on the venous side is measured by the associated pressure sensor 186 on the front face of the module 130 (shown in FIG. 9).

In certain implementations, a drug, such as heparin, is injected into the blood via the drug delivery line 174 by activating the drug pump 192. Injecting heparin into the blood can help to prevent blood clots from forming within the blood circuit. Other types of drugs can alternatively or additionally be injected from the syringe 178 into the blood circuit. Examples of such drugs include vitamin D and iron supplements, such as Venofer® and Epogen®.

Next, the blood flows through the entry port 142 of the air release device 112 in which any gas, such as air, in the blood can escape. When the blood enters the chamber 116 of the air release device 112, the blood forces the saline at the bottom of the chamber 116, which remains in the chamber 116 from the priming procedure, through the exit port 144 of the air release device 112. However, the blood does not displace all of the saline within the chamber 116. Because of the size and shape of the chamber 116, the blood enters the chamber 116 and only traverses part of the height of the chamber 116 before flowing back down and exiting the exit port 144. The interface 152 (shown in FIG. 5) between the saline and the blood delineates the furthest extent of the vast majority of the blood within the chamber 116. Because blood and saline are not immiscible, there is some amount of mixing between the two fluids around the interface 152.

The saline substantially prevents the blood from contacting the membrane 148 of the vent assembly 114. However, some blood can be present in the saline without hindering treatment. That is, the saline need not be completely free of blood for the air release device 112 to both allow gas (e.g., from air bubbles in the blood) to vent from the blood circuit and retain the liquid within the blood circuit. The solution that is mostly saline protects the membrane 148 of the vent assembly 114 from becoming coated with protein, which could clog the vent assembly 114 and reduce the ability of the air release device 112 to vent air and other gases from the chamber 116 of the air release device 112 to the atmosphere. If the chamber 116 of the release device 112 is sufficiently elongated, the blood does not mix with the saline at the top portion of the chamber 116 because the saline remains relatively stagnant as the blood flows through the chamber 116.

Any unbound gas, or air, that is in the blood, such as air that is introduced by the dialyzer 110 or syringe 178, rises as tiny air bubbles within the blood and saline until the air eventually vents out through the vent assembly 114. The blood travels up and over the dam 146 rather than straight across the bottom of the chamber 116 and out the exit port 144. By directing the flow of blood upwards, the blood with air is not able to flow in and directly back out of the chamber 116 without flowing upwards to at least a height greater then the height of the dam 146. The surface area of the dam 146 and the inner walls of the chamber 116 encourage air, including microbubbles, to separate from the blood and exit the blood circuit through the vent assembly 114.

After exiting the air release device 112, the blood travels through the venous patient line 108 and back to the patient.

Turning now to the dialysate circuit illustrated on the right side of FIG. 11, during hemodialysis, fresh dialysate is pumped into the dialysate circuit from the dialysate container 124 via the dialysate supply line 126 by running the dialysate pump 204. The fresh dialysate enters the second chamber half 220 of the balancing device 206. As spent dialysate enters the first chamber half 218 of the balancing device 206, the fresh dialysate is forced out of the second chamber half 220 and toward the dialyzer 110 via the dialysate line 216. The dialysate passes through the dialyzer 110 at the same time that the patient's blood is passed through the dialyzer 110 on an opposite side of the semipermeable structure of the dialyzer 110. As a result, toxins, such as urea, are transferred across a permeable structure (e.g., permeable membrane and/or permeable microtubes) of the dialyzer 110 from the patient's blood to the dialysate, and those toxins collect in the dialysate forming spent dialysate. The spent dialysate exiting the dialyzer 110 is circulated through the dialysate circuit to the equalizing chamber 210. The dialysate pump 212 draws spent dialysate from the equalizing chamber 210 and delivers it to the first chamber half 218 of the balancing device 206. As the spent dialysate fills the first chamber half 218, fresh dialysate within the second chamber have 220 is delivered to the dialyzer 110. As the second chamber half 220 is subsequently refilled with fresh dialysate, the spent dialysate within the first chamber half 218 is forced out of the balancing device 206 and into a drain via the drain line 128. The balancing device 206 balances the dialysate entering the dialysate circuit with the dialysate exiting the dialysate circuit to ensure that a substantially constant volume of dialysate remains within the dialysate circuit when ultrafiltration is not being performed.

In certain treatments, an ultrafiltration process is performed to remove excess fluid from the patient's blood. During ultrafiltration, a pressure gradient is created across the permeable structure between the dialysate side and the blood side of the dialyzer 110 by running the ultrafiltration pump 214. As a result, fluid is drawn across the semipermeable structure of the dialyzer 110 from the blood circuit to the dialysate circuit. Spent dialysate, including the toxins and excess fluid drawn from the patient, is drawn from the equalizing chamber 210 by the ultrafiltration pump 214 and is delivered to the drain via the ultrafiltration line 129.

It is also advantageous to periodically test the vent assembly 114 of the air release device 112 during the hemodialysis treatment. By doing this, it is possible to detect damage that might occur to the vent assembly 114 during treatment. For example, such a testing procedure can be used to detect whether the membrane 148 of the vent assembly 114 has ruptured causing liquid to contact the vent structure 150 and thus causing the vent structure 150 to self-seal. Such a testing procedure can also be used to detect whether protein has built up on the membrane 148 of the vent assembly 114 due to contact with blood and, as a result, significantly diminished the ability of the vent assembly 114 to allow air to pass therethrough.

In order to test the air release device 112 during hemodialysis treatment, the blood pump 132 and the dialysate pumps 204, 212 are temporarily stopped, the venous patient line 108 is clamped, the ultrafiltration pump 214 is turned on, and the blood level within the chamber 116 of the air release device 112 is monitored. Typically, the test lasts no more than about 60 seconds (e.g., no more than about 15 seconds, about 10-15 seconds), and thus the blood pump 132 can be stopped without negatively affecting the blood in the blood circuit. A drop in the blood level within the chamber 116 below the level of the level detector 182 after running the ultrafiltration pump 214 for a desired time and at a desired speed indicates that the vent assembly 114 of the air release device 112 is functioning properly, while a drop in the blood level to a point above the height of the level detector 182 or no drop at all in the blood level indicates that the vent assembly 114 is not functioning properly. If the vent assembly 114 is determined to be functioning properly, the treatment simply resumes. If, however, the vent assembly 114 is determined to be working improperly, the operator of the hemodialysis system 100 is alerted via the touch screen 118 and the speaker 122 so that remedial action can be taken. In response to such an alert, the operator can repair or replace the air release device 112 using any of the various techniques described above. It is advantageous for the user to be able to repair the air release device 112 under these circumstances by simply replacing the vent assembly 114. This allows the user to repair the air release device 112 with only a minor interruption to the remainder of the blood circuit, which, contains blood during treatment.

In certain implementations, the above-described test procedure is automated and is performed regularly throughout the treatment. Alternatively, the control unit of the hemodialysis machine 102 can be adapted to simply alert the user (e.g., via the touch screen 118 and/or the speaker 122) when it is time to manually perform the test. In some implementations, the test is performed at least two times (e.g., at least five times) during the treatment. The test can, for example, be performed at least every 60 minutes (e.g., every 30 minutes, every 15 minutes) throughout the treatment.

After completing the patient's treatment, the dialysate within the dialysate circuit is pumped to the drain using the dialysate pump 212 and/or the ultrafiltration pump 214. The blood component set 104 is then disconnected from the module 130 of the hemodialysis machine 102 and discarded, and the dialysate circuit is sterilized in preparation for a subsequent treatment.

While certain embodiments have been described above, other embodiments are possible.

While the methods described above involve using the measured liquid level in the air release device 112 to determine whether the vent assembly 114 of the air release device 112 is working properly, other techniques can alternatively or additionally be used. In some implementations, for example, the blood pressure measured by the venous pressure transducer 186 is used to determine whether the vent assembly 114 is functioning properly. If the vent assembly 114 is not functioning properly, then a desired amount of air would not be pulled into the blood circuit via the vent assembly 114 when applying vacuum pressure to the chamber 116 of the air release device 112. As a result, the pressure within the blood circuit would decrease and the blood lines forming the blood circuit might start to collapse. Thus, a pressure reduction detected at the venous pressure transducer 186 of greater than a certain value while drawing a vacuum on the chamber 116 of the air release device 112 in the manner discussed above indicates that the vent assembly 114 of the air release device 112 is not functioning properly. In some implementations, for example, a pressure reduction of about 100 mm Hg or more indicates that the vent assembly 114 is not working properly. A pressure drop of less than a certain value, on the other hand, indicates that the vent assembly 114 is working properly. In certain implementations, for example, a pressure reduction of less than about 10 mm Hg (e.g., about 0 mm Hg) indicates that the vent assembly 114 is working properly or sufficiently.

In some implementations, the level detector 182 and the venous pressure transducer 186 are used in combination to determine whether the vent assembly 114 of the air release device 112 is functioning properly. Thus, even if one of the level detector 182 and venous pressure transducer 186 were not working properly, a malfunctioning vent assembly 114 could still be detected. Alternatively, the control unit of the hemodialysis machine 102 can be adapted so that no alarm is activated unless both the level detector 182 and the venous pressure transducer 186 indicate that the vent assembly 114 is not functioning properly. This can help to ensure that a malfunctioning vent assembly 114 is not erroneously identified to the operator of the system 100.

While the arterial pressure sensor 184 and the corresponding arterial pressure sensor capsule 154 have been described as being arranged upstream of the blood pump 132 to measure a pre-pump arterial pressure, they can alternatively be positioned downstream of the blood pump 132 to measure a post-pump arterial pressure, or an additional arterial pressure sensor and arterial pressure sensor capsule can be positioned downstream of the blood pump 132 to measure a post-pump arterial pressure. In implementations in which a post-pump arterial pressure sensor is provided, the post-pump arterial pressure sensor can be used instead of or in addition to the venous pressure transducer 186 to detect whether the vent assembly 114 of the air release device 112 is functioning properly. For example, with the venous patient line 108 clamped and the blood pump 132 turned off, the ultrafiltration pump 214 can be operated to draw a vacuum on the air release device 112 and the arterial pressure sensor can monitor the pressure within the blood circuit. Upon detecting that the pressure within the blood circuit has dropped below a certain level, the arterial pressure sensor can transmit a signal to that effect to the microprocessor of the hemodialysis machine 102, which can activate an audio and/or visual alarm to alert the operator of the system that the air release device 112 is not functioning properly. In response, the operator of the system can take any of the various different remedial actions described above.

While some of the above methods use the pressure sensed at the venous pressure transducer 186 or the pressure sensed at an arterial pressure sensor located downstream of the blood pump 132 to determine whether the vent assembly 114 of the air release device is working properly, in some implementations, the trans-membrane pressure (i.e., the pressure differential between the blood circuit and the dialysate circuit) is used to determine whether the vent assembly 114 is functioning properly. The measured transvenous membrane can be compared with the pressure ranges discussed above with respect to the venous and arterial pressure transducers in order to determine whether the air release device 112 is venting properly.

While methods discussed above involve operating the ultrafiltration pump 214 to apply vacuum pressure to the air release device 112, vacuum pressure can alternatively or additionally be applied to the air release device 112 using other techniques. In certain implementations, for example, the vacuum pressure is applied to the air release device 112 by running the dialysate pumps 204, 212, rather than the ultrafiltration pump 214. In some such implementations, the dialysate pump 212 is operated while allowing a discrete amount of fluid to exit the dialysate circuit through the first chamber half 218 of the balancing device 206 but not allowing fluid to enter the dialysate circuit via the second chamber half 220 of the balancing device. The dialysate pump 204 remains off as the fluid exits the dialysate circuit to ensure that no additional fluid is introduced into the dialysate circuit. The discrete amount of fluid that is removed from the dialysate circuit is dictated by the volume of the balancing device 206. In some implementations, the balancing device 206 has a volume of 30 cc such that 30 cc of fluid is removed from the dialysate circuit during this procedure. Because fluid is removed from the dialysate circuit without being replaced, a negative pressure is created in the dialysate circuit. This negative pressure is also applied to the blood circuit via the semi-permeable membrane of the dialyzer 110, and thus acts on the air release device 112. While this negative pressure is applied to the air release device 112, the air release device 112 can be tested in the manner described above. After testing the air release device 112, the dialysate pump 204 is operated (while the dialysate pump 212 remains off) to pump additional fluid into the dialysate circuit to restore the fluid volume of the dialysate circuit to its original value. Because the volume of the balancing device 206 dictates the amount of fluid that is added to the dialysate circuit, it can be ensured that the same amount of fluid that was previously removed from the dialysate circuit is now added back into the dialysate circuit.

As an alternative to controlling the amount of fluid delivered to and from the dialysate circuit based on the volumetric capacity of the balancing device 206, other techniques can be used. In certain implementations, for example, the pressure transducer 208 is used to ensure that the same volume of fluid drawn from the dialysate circuit is later added back into the dialysate circuit. In such implementations, when it is time to test the air release device 112 by applying negative pressure to the blood circuit, a reading of the pressure transducer 208 is taken. This pressure reading corresponds to the total volume of fluid within the dialysate circuit at that time. Then, the dialysate pump 212 is operated (with the dialysate pump 204 turned off) to remove fluid from the dialysate circuit. While doing this, the valves associated with the balancing device 206 are controlled in a manner to allow fluid to readily flow through the first chamber half 218 of the balancing device 206 while preventing fluid from flowing through the second chamber half 220 of the balancing device 206. The removal of fluid from the dialysate circuit causes a pressure drop within the dialysate and blood circuits, which allows the air release device 112 to be tested in the manner described above. After testing the air release device 112, the dialysate pump 204 is turned on and the dialysate pump 212 is turned off. In addition, the valves associated with the balancing device 206 are controlled in a manner to allow fluid to readily flow through the second chamber half 220 of the balancing device 206 while preventing fluid from flowing through the first chamber half 218 of the balancing device 206. The dialysate pump 204 continues to run until the reading of the pressure transducer 208 is the same as the reading taken before the fluid was removed from the dialysate circuit. The identical pressure readings indicate that the total volume of fluid in the dialysate circuit is equal to the total volume of fluid that was present in the dialysate circuit prior to removing fluid from the dialysate circuit. Because the amount of volume removed from and added back into the dialysate circuit is not limited to the volumetric capacity of the balancing device 206 using this technique, larger volumes of fluid can be removed from the dialysate circuit, thereby resulting in the ability to apply increased levels of negative pressure to the air release device 112.

In some implementations, the drug pump 192 is used to draw a vacuum on the chamber 116 of the air release device 112. The drug pump 192 is operated in a manner to draw liquid out of the blood circuit rather than being operated in a manner to inject liquid (e.g., drug from the syringe 178) into the blood circuit. To do this, the drug pump 192 is simply run in the opposite direction than it is run to deliver drug to the blood circuit. Prior to performing the test procedure, the syringe 178 containing the liquid drug is replaced with an empty syringe such that the liquid pulled out of the blood circuit can be collected in the empty syringe. To test the vent assembly 114 of the air release device 112, the blood pump 132, the dialysate pumps 204, 212, and the ultrafiltration pump 214 are turned off, the venous patient line 108 is clamped, and the drug pump 192 is operated in a manner to pull liquid from the blood circuit into the empty syringe. Because the blood pump 132 is stopped thereby acting as a closed clamp along the arterial patient line 106 and the venous patient line 108 is clamped the syringe pump 192 applies a vacuum pressure to the chamber 116 of the air release device 112 as it pulls liquid into the empty syringe.

In certain implementations, the blood pump 132 is operated in a manner to apply vacuum pressure to the air release device 112. In particular, rather than running the blood pump 132 in a forward direction such that liquid within the blood circuit is pumped in the direction from the arterial patient line 106 toward the dialyzer 110, the blood pump 132 is operated in a reverse direction such that liquid within the blood circuit is pumped in the direction from the dialyzer 110 toward the arterial patient line 106. To draw a vacuum on the air release device 112 while operating the blood pump 132 in the reverse direction, the venous patient line 108 is clamped and the various pumps of the dialysate circuit are turned off. As a result, when the blood pump 132 is operated in the reverse direction, liquid is pulled from the chamber 116 of the air release device 112 toward the dialyzer 110 and the blood pump 132. Because the venous patient line 108 is clamped, the causes a vacuum to be drawn on the chamber 116 of the air release device 112 and can thus be used to test the functionality of the vent assembly 114 of the air release device 112 using any of the various techniques described herein.

While certain methods discussed above involve clamping the venous patient line 108 to pull a vacuum on the chamber 116 of the air release device 112, the patient's arm to which the arterial and venous patient lines 106, 108 can alternatively be lowered during the test procedure. Lowering the patient's arm would decrease venous pressure and could achieve a result similar to clamping the venous patient line 108.

While some of the above methods have been described as temporarily halting the flow of liquid through the blood circuit or a portion of the blood circuit while operating one of the pumps connected to the dialysate circuit to draw a vacuum on the chamber 116 of the air release device 112, in some implementations, the flow of liquid through the blood circuit is maintained. In such implementations, the pump(s) connected to the dialysate circuit that are used to draw the vacuum (e.g., the dialysate pumps 204, 212 or the ultrafiltration pump 214) are simply operated at a high enough rate to draw a vacuum on the blood circuit notwithstanding the flow of liquid through the blood circuit. Similarly, for those methods above that describe halting the flow of liquid through the dialysate circuit while the blood pump 132 or the drug pump 192 are operated in reverse to pull a vacuum on the chamber 116 of the air release device 112, it should be appreciated that the flow of liquid through the dialysate circuit need not be stopped. In such cases, the flow of liquid through the dialysate circuit would increase the vacuum pressure applied to the chamber 116 of the air release device 112.

While certain methods above involve forcing air out of the chamber 116 of the air release device 112 by running the blood pump 132 with the venous patient line 108 clamped, other techniques can alternatively or additionally be used to force air out of the air release device 112. For example, in those implementations in which the drug pump 192 is operated in reverse to pull a vacuum on the chamber of the air release device 112, the syringe pump could subsequently be operated in the normal direction with the venous patient line 108 clamped. This would cause any liquid drawn into the syringe by running the drug pump 192 in reverse to be forced back into the blood circuit and would create a positive pressure within the blood circuit. As a result, any air within the chamber 116 of the air release device 112 would be expelled to the atmosphere via the vent assembly 114. As another example, the dialysate pumps 202, 214 and/or the ultrafiltration pump 214 can be operated in reverse with the venous patient line 108 clamped in order to create a positive pressure within the blood circuit and force any air within the chamber 116 of the air release device 112 to the atmosphere via the vent assembly 114.

While the methods described above involve activating an audio alarm and visual arm in response to detecting a malfunctioning device, an audio alarm alone or a visual alarm alone can alternatively be used to alert the operator of the system to the malfunctioning device.

While certain visual alarms have been described as being displayed via the touch screen 118, the visual alarms can be displayed using other types of devices. For example, in implementations in which the dialysis machine includes a traditional screen (i.e., a non-touch screen) along with a separate device, such as a keyboard, for inputting data, the visual alarm can be displayed via the traditional screen.

While the level detector 182 has been described as an ultrasonic device configured to emit and receive ultrasonic signals, any of various other types of devices capable of detecting a level of liquid within the chamber 116 of the air release device 112 can be used. Examples of such devices include, among other things, light sensors.

While the module 130 has been described as including pressure transducers 184, 186 to detect fluid pressure within the blood circuit, any of various other types of pressure sensors can be used to measure this fluid pressure. In some implementations, for example, inline pressure transducers configured to measure positive and negative pressure on the line itself may be used.

While the drug pump 192 has been described as a syringe pump, other types of drug pumps can be used. In certain implementations, for example, the drug pump is a peristaltic pump. During use of such a peristaltic pump, a drug delivery line of a blood component set is connected to a drug vial (e.g., a heparin vial) and operatively positioned within a housing of the pump in a manner such that rolling members of the pump operatively engage the drug delivery line. The pump can be operated in a first direction to inject the drug into the blood passing through the blood lines of the blood component set. Alternatively, the drug delivery line can be connected to an empty vial or a drain and the pump can be operated in an opposite direction to draw liquid passing through the blood lines into the vial or drain via the drug delivery line.

While the vent assembly 114 of the air release device 112 has been described as including the membrane 148 and vent structure 150, other types of vents can be used. In some implementations, for example, the vent of the air release device includes only the membrane.

In some implementations, the air release device 112 and at least one of the other blood components and blood lines (e.g., all of the other blood components and blood lines) are incorporated into an integrated blood component set. The various components of the integrated blood circuit can be formed together in one assembly or integrated molding rather than discrete separate or modular devices. The integrated blood component set can be adapted to removably seat into the module 130 of the hemodialysis machine 102 in a manner similar to the blood component set 104 described above.

While the various blood components have been described as being either secured to the carrier body 134 or incorporated into an integrated blood component set, the blood components can alternatively be connected to one another by blood lines alone. In such implementations, the blood components would be individually secured to the hemodialysis machine 102 (e.g., the module 130 of the hemodialysis machine 102) prior to treatment. The functionality of the blood components would be similar to the functionality of those blood components discussed above.

While the dialysate circuit has been described as being partially integrated with the hemodialysis machine 102, the dialysate circuit can alternatively be formed by a dialysate component set that can be removably secured to a hemodialysis machine during use. In some implementations, the dialysate component set is in the form of a cassette that can be inserted into a drawer of the hemodialysis machine in a manner such that the cassette operatively engages components of the hemodialysis machine when the drawer is closed. Such a dialysate component sets is described, for example, in U.S. patent application No. 61/231,220, entitled "Dialysis Systems, Components, and Methods" and filed on Aug. 4, 2009, which is incorporated by reference herein.

While the hemodialysis machine 102 has been described as including a touch screen, it should be appreciated that any of the hemodialysis machines described herein can alternatively be provided with a conventional screen and an associated control panel or keyboard to allow the user to input data. Alternatively or additionally, the hemodialysis machine can be equipped with a scratch pad and/or touch buttons that permit the user to input data.

While the various instruments that the cooperate with the blood components and blood lines to cause blood flow and monitor blood flow through the blood circuit has been described as being part of a module of the hemodialysis machine, it should be appreciated that these instruments could be integrated into the hemodialysis machine.

Figure 12:
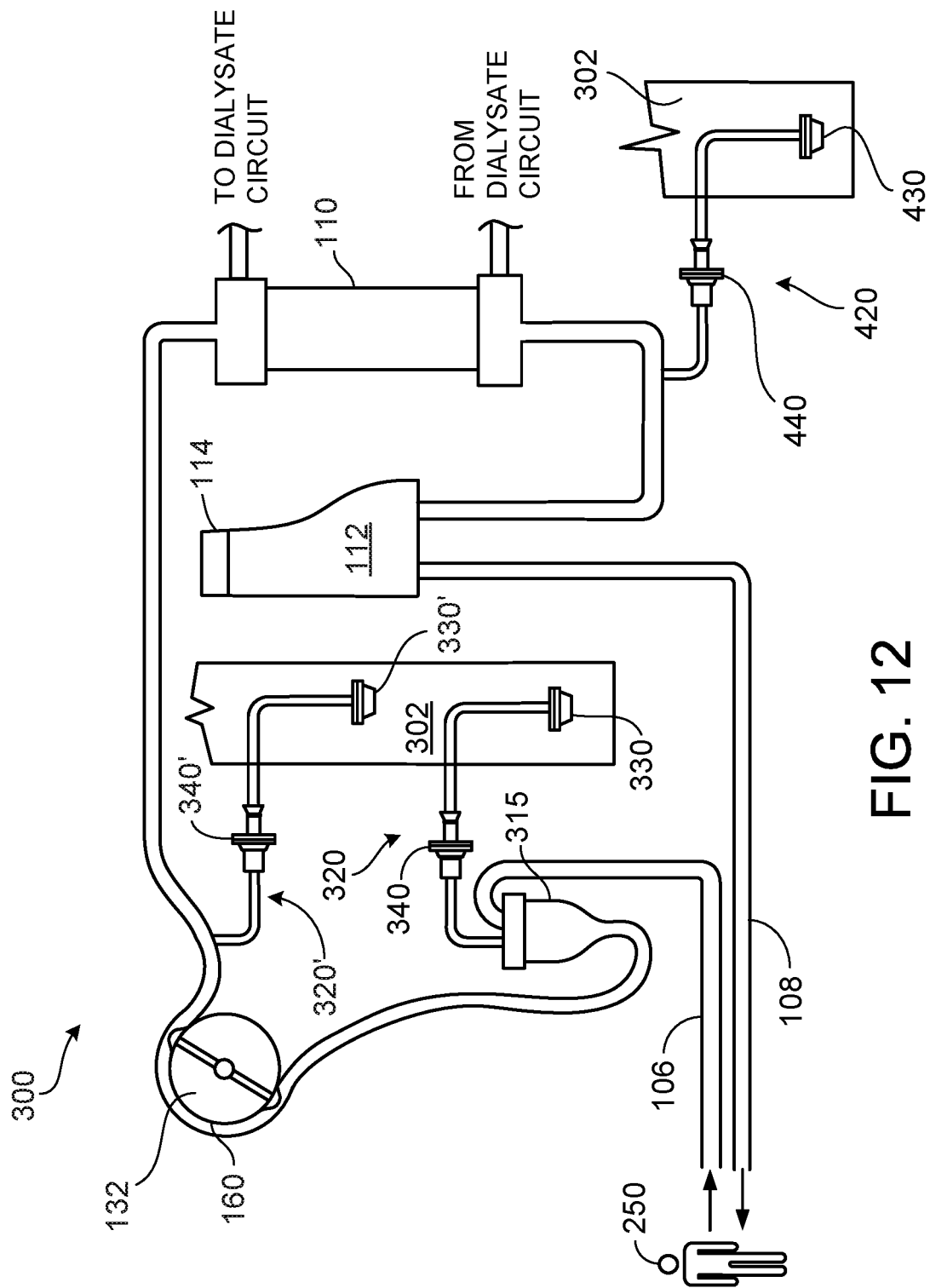
FIG. 12 is a schematic of a hemodialysis system including a blood component set with a pressure sensing blood line having a transducer protector connected to a pressure transducer of a hemodialysis machine.

While the test methods described above have been discussed with respect to air release devices in hemodialysis systems, similar methods can be used to test other types of devices that include vents to allow air and/or other gases to enter and/or exit the devices. FIG. 12, for example, is a schematic of a hemodialysis system 302 that includes a hemodialysis machine 302 to which a blood component set including a pre-pump arterial pressure sensor assembly 320, a post-pump arterial pressure sensor assembly 320', and a venous pressure sensor assembly 420 is connected. Each of the pressure sensor assemblies 320, 320', 420 includes a fluid line including a pressure transducer protector 340, 340', 440. The pressure sensor assemblies 320, 320', 420 include pressure transducers 330, 330', 430 that are secured to the hemodialysis machine 302. Each of the transducer protectors 340, 340', 440 includes a body that forms a fluid pathway and a vent assembly positioned along the fluid pathway. This arrangement allows gas (e.g., air) to pass through the vent assemblies of the transducer protectors 340, 340', 440, while inhibiting the passage of blood therethrough. As a result, the pressure transducers 330, 330', 430 do not come into contact with blood during treatment. The pressure transducers 330, 330', 430 measure changes in air pressure, which can be used to determine the pressure of the blood within the blood circuit.

The vent assemblies of the transducer protectors 340, 340', 440 help to protect the pressure transducers 330, 330', 430, and the dialysis machine 302 on which those transducers are mounted, from direct contact with blood flowing within the blood circuit. Vent assemblies similar to those discussed herein with respect to the air release devices can be used in the transducer protectors 340, 340', 440. In some implementations, each of the vent assemblies includes a microporous membrane (similar to the membrane 148 described above) and a self-sealing vent structure (similar to the vent structure 150 described above) that is positioned between the microporous membrane and the pressure transducer 330, 330', 430 and is designed to automatically seal shut upon coming into contact with blood. Thus, should the microporous membrane rupture and allow blood to pass therethrough, the vent structure will seal and will thus inhibit (e.g., prevent) the dialysis machine 302 from becoming contaminated.

During hemodialysis, blood flows from the patient 250 through the arterial patient line 106 to a drip chamber 315. Blood drips into the drip chamber 315 where a connecting tube from the drip chamber 315 connects to the hemodialysis machine 302 via the pre-pump arterial pressure sensor assembly 320. The blood pump 132 is used to pump the blood from the drip chamber 315 to the dialyzer 110. The post-pump arterial pressure assembly 320' is connected to the blood line leading from the blood pump 132 to the dialyzer 110. The pre-pump arterial pressure sensor assembly 320 and post-pump arterial pressure sensor assembly 320' are used to determine the pressure of the blood on the arterial side of the blood circuit. After passing through the dialyzer 110, the blood flows to the air release device 112 in which gas (e.g., air) in the blood can escape before the blood continues to the patient 250. The venous pressure sensor assembly 420 is connected to the blood line leading from the dialyzer 110 to the air release device 110. The venous pressure sensor assembly 420 is used to determine the pressure of the blood on the venous side of the blood circuit. After leaving the air release device 110, the blood travels through the venous patient line 108 and back to the patient 250.

It is beneficial to test the functionality of the vent assemblies of the transducer protectors 340, 340', 440 before treatment begins (e.g., right after priming the blood circuit) and/or during treatment. To determine whether the vent assemblies of the transducer protectors 340, 340', 440 are functioning properly, methods similar to those discussed above can be used.

To test the vent assemblies of the transducer protectors 340', 440, the pressure sensor assembly 320', 420 including the transducer protector 340', 440 to be tested is disconnected from the dialysis machine 302 and a vacuum pressure is applied to the transducer protector 340', 440 to be tested. While applying vacuum pressure to the transducer protector 340', 440 being tested, the pressure within the blood circuit is monitored by the other of the pressure sensor assemblies 320', 420, which remains connected to the dialysis machine 302, to determine whether air is being pulled through the vent assembly as a result of the vacuum pressure. If air is being pulled through the vent assembly, the pressure within the blood circuit, as detected by the pressure transducer 330', 430 of the connected pressure sensor assembly 320', 420, will remain within a desired pressure range and this will indicate that the vent assembly is functioning properly. If air is not being pulled through the vent assembly, the pressure within the blood circuit will drop below a minimum desired pressure and this will indicate that the vent assembly is not functioning properly.

Any of the various vacuum generating techniques described above can be used to apply vacuum pressure to the transducer protectors 340', 440. For example, the blood pump 132 can be turned off, the venous patient line 108 or the line connecting the dialyzer 110 to the air release device 112 can be clamped off, and the ultrafiltration pump and/or dialysate pumps in the dialysate circuit can be operated to draw fluid from the blood circuit to the dialysate circuit and thus create vacuum pressure within the portion of the blood circuit between the blood pump 132 and the clamp. Alternatively or additionally, the blood pump 132 and/or the drug pump can be operated in reverse while the venous patient line 108 or the line connecting the dialyzer 110 to the air release device 112 is clamped.

To test the vent assembly of the transducer protector 340, a vacuum pressure is applied to the transducer protector 340 by clamping the arterial patient line 106 and operating the blood pump 132 to draw fluid out of the drip chamber 315 toward the blood pump 132. At the same time, a level detector on the hemodialysis machine is used to detect the liquid level within the drip camber 315. The level detector and the drip chamber 315 can, for example, be arranged in a manner similar to the level detector 182 and the air release device 112. If air is being pulled through the vent assembly of the transducer protector 340, the liquid level within the drip chamber 315 will drop below the height of the level detector. This will indicate that the vent assembly is functioning properly. If air is not being pulled through the vent assembly, the liquid level within the drip chamber 315 will remain at or above the height of the level detector. This will indicate that the vent assembly is not functioning properly.

While the above testing methods have been described with respect to hemodialysis systems, similar methods can be used to test vented devices of any of various other types of systems, including peritoneal dialysis systems, blood transfusion systems, cardiopulmonary bypass systems, drug infusion systems, etc.

Other embodiments are within the scope of the following claims.

What is claimed is:

1. A dialysis system, comprising:
    an air release device comprising a vent;
    a level detector configured to detect a level of fluid within the air release device; and
    a control unit connected to the level detector, wherein the control unit is programmed to
        apply a vacuum pressure to the air release device, and then
        determine whether the air release device is functioning properly based on the detected level of fluid within the air release device when the vacuum pressure is applied to the air release device.

2. A dialysis system, comprising:
    an air release device comprising a vent;
    a fluid line fluidly connected to the air release device;
    a pressure sensor configured to measure pressure of fluid within the fluid line; and
    a control unit connected to the pressure sensor, wherein the control unit is configured to
        apply a vacuum pressure to the air release device, and then
        determine whether the air release device is functioning properly based on the measured pressure of fluid within the fluid line when the vacuum pressure is applied to the air release device.

3. The dialysis system of claim 1, wherein:
    the air release device comprises a housing defining a liquid chamber,
    the vent is disposed at an end of the liquid chamber, and
    the vacuum pressure is applied to the liquid chamber of the air release device.

4. The dialysis system of claim 3, wherein the control unit is programmed to determine that the vent of the air release device is functioning properly based on determining that air is being drawn into the liquid chamber through the vent.

5. The dialysis system of claim 1, wherein the level detector comprises a transmitter configured to emit ultrasonic signals and a receiver adapted to receive ultrasonic signals.

6. The dialysis system of claim 1, further comprising:
    first and second fluid lines connected to the air release device, and
    a pump configured to circulate fluid from the first fluid line to the air release device to the second fluid line during dialysis treatment.

7. The dialysis system of claim 6, wherein the control unit is configured to close off the second fluid line and operate the pump in a manner to circulate fluid from the second fluid line to the air release device to the first fluid line to apply the vacuum pressure to the air release device.

8. The dialysis system of claim 6, wherein the pump is a drug pump configured to introduce fluid into the first fluid line when operated in a first direction and is configured to draw fluid out of the first fluid line when operated in a second direction.

9. The dialysis system of claim 8, wherein the control unit is programmed to operate the pump in the second direction to apply the vacuum pressure to the air release device.

10. The dialysis system of claim 1, further comprising:
    a dialyzer fluidly connected to the air release device,
    a first fluid line connecting a first pump to the dialyzer, and
    a second fluid line connecting a second pump to the dialyzer,
    wherein the first pump is configured to circulate a first fluid from the first fluid line through the dialyzer during dialysis treatment, and
    wherein the second pump is configured to circulate a second fluid from the dialyzer through the second fluid line during the dialysis treatment.

11. The dialysis system of claim 10, wherein the control unit is programmed to stop the first pump to close off the first fluid line and operate the second pump in a manner to circulate fluid from the second fluid line to the dialyzer to apply the vacuum pressure to the air release device.

12. The dialysis system of claim 2, wherein:
    the air release device comprises a housing defining a liquid chamber, and
    the vent is disposed at an end of the liquid chamber.

13. The dialysis system of claim 12, wherein the control unit is programmed to determine that the vent of the air release device is functioning properly based on determining that air is being drawn into the liquid chamber through the vent.

14. The dialysis system of claim 2, wherein the pressure sensor comprises a pressure transducer.

15. The dialysis system of claim 2, wherein the fluid line is a first fluid line connected to the air release device, and the dialysis system further comprises:
    a second fluid line connected to the air release device, and
    a pump configured to circulate fluid from the first fluid line to the air release device to the second fluid line during dialysis treatment.

16. The dialysis system of claim 15, wherein the control unit is programmed to close off the second fluid line and operate the pump in a manner to circulate fluid from the second fluid line to the air release device to the first fluid line to apply the vacuum pressure to the air release device.

17. The dialysis system of claim 15, wherein the pump is a drug pump configured to introduce fluid into the first fluid line when operated in a first direction and is configured to draw fluid out of the first fluid line when operated in a second direction.

18. The dialysis system of claim 17, wherein the control unit is programmed to operate the pump in the second direction to apply the vacuum pressure to the air release device.

19. The dialysis system of claim 2, further comprising:
    a dialyzer fluidly connected to the air release device,
    a first fluid line connecting a first pump to the dialyzer, and
    a second fluid line connecting a second pump to the dialyzer,
    wherein the first pump is configured to circulate a first fluid from the first fluid line through the dialyzer during dialysis treatment, and
    wherein the second pump is configured to circulate a second fluid from the dialyzer through the second fluid line during the dialysis treatment.

20. The dialysis system of claim 19, wherein the control unit is programmed to stop the first pump to close off the first fluid line and operate the second pump in a manner to circulate fluid from the second fluid line to the dialyzer to apply the vacuum pressure to the air release device.

21. The dialysis system of claim 1, wherein the control unit is programmed to
   apply vacuum pressure to a chamber of the air release device,
   after applying the vacuum pressure to the air release device, detect the level of fluid within the chamber of the air release device using the level detector, and
   determine, based on the detected level of fluid in the chamber of the air release device, whether air is being drawn into the chamber through the vent.

22. The dialysis system of claim 2, wherein the control unit is programmed to
   apply vacuum pressure to a chamber of the air release device,
   after applying the vacuum pressure to the air release device, measure the pressure within the fluid line using the pressure sensor, and
   determine, based on the measured pressure in the fluid line, whether air is being drawn into the chamber through the vent.

* * * * *

UNITED STATES PATENT AND TRADEMARK OFFICE
CERTIFICATE OF CORRECTION

PATENT NO.         : 9,821,107 B2
APPLICATION NO.    : 14/965103
DATED              : November 21, 2017
INVENTOR(S)        : Colin Weaver and Martin Joseph Crnkovich It is certified that error appears in the above-identified patent and that said Letters Patent is hereby corrected as shown below:

In the Specification

Column 1, Lines 8 and 9, before "application" delete "application No."

Signed and Sealed this
Twentieth Day of February, 2018

Andrei Iancu
*Director of the United States Patent and Trademark Office*